(12) United States Patent
Borovinskaya et al.

(10) Patent No.: US 11,197,852 B2
(45) Date of Patent: Dec. 14, 2021

(54) CONTINUOUS DELIVERY OF LENALIDOMIDE AND OTHER IMMUNOMODULATORY AGENTS

(71) Applicant: Starton Therapeutics, Inc., New York, NY (US)

(72) Inventors: Marina Borovinskaya, East Brunswick, NJ (US); Fotios Plakogiannis, Whitestone, NY (US); Nisarg Modi, Bellerose, NY (US); Tamanna Lather, Jersey City, NJ (US); Rod L. Hartwig, Sloatsburg, NY (US); James C. Oliver, Raleigh, NC (US); Yuliya Levintova, Brooklyn, NY (US)

(73) Assignee: Starton Therapeutics, Inc., Paramus, NJ (US)

( * ) Notice: Subject to any disclaimer, the term of this patent is extended or adjusted under 35 U.S.C. 154(b) by 0 days.

(21) Appl. No.: 16/854,810

(22) Filed: Apr. 21, 2020

(65) Prior Publication Data

US 2020/0330445 A1 Oct. 22, 2020

Related U.S. Application Data

(60) Provisional application No. 62/945,028, filed on Dec. 6, 2019, provisional application No. 62/837,057, filed on Apr. 22, 2019.

(51) Int. Cl.
*A61K 31/454* (2006.01)
*A61K 47/10* (2017.01)
(Continued)

(52) U.S. Cl.
CPC ............ *A61K 31/454* (2013.01); *A61K 47/10* (2013.01); *A61K 9/0021* (2013.01); *A61K 9/7023* (2013.01)

(58) Field of Classification Search
None
See application file for complete search history.

(56) References Cited

U.S. PATENT DOCUMENTS 6,124,322 A * 9/2000 Bjoerkman .......... A61K 9/0019
514/323
2007/0208057 A1 * 9/2007 Zeldis ....................... A61P 1/16
514/323

(Continued)

FOREIGN PATENT DOCUMENTS

WO WO 2005/046593 A2 5/2005
WO WO-2017216738 A1 * 12/2017 ............. A61K 47/08
WO WO 2018/138737 A1 8/2018

OTHER PUBLICATIONS

REVLIMID® Prescribing Information, revised Feb. 2017, 45 pages. (Year: 2017).*

(Continued)

*Primary Examiner* — Daniel R Carcanague
(74) *Attorney, Agent, or Firm* — Dority & Manning, P.A.

(57) ABSTRACT

Provided are methods for continuously administering to a subject in need of treatment a formulation comprising an immunomodulatory imide compound. In some embodiments, the method are for use in treating multiple myeloma, transfusion-dependent anemia due to low- or intermediate-1-risk myelodysplastic syndromes, mantle cell lymphoma, hematologic cancers, or solid tumor cancers.

18 Claims, 7 Drawing Sheets

(51) Int. Cl.
*A61K 9/00* (2006.01)
*A61K 9/70* (2006.01)

(56) References Cited

U.S. PATENT DOCUMENTS

2010/0278779 A1* 11/2010 Zeldis ................. A61K 31/454
424/85.2
2017/0038387 A1* 2/2017 Gandhi ................ A61K 31/517
2019/0060221 A1* 2/2019 Joharapurkar ......... A61K 47/10

OTHER PUBLICATIONS

Blum; Journal of Clinical Oncology 2010, 28, 4919-4925. (Year: 2010).*
Carlson; Annals of Internal Medicine 1983, 99, 823-833. (Year: 1983).*
Chen; J Clin Oncol. 2011, 29, 1175-1181. (Year: 2011).*
Eisen; British Journal of Cancer 2000, 82, 812-817. (Year: 2000).*
Franks; Lancet 2004, 363, 1802-1811. (Year: 2004).*
Galustian; Expert Opinion on Pharmacotherapy 2009, 10, 125-133. (Year: 2009).*
Pineda-Roman; Leukemia 2008, 22, 1419-1427. (Year: 2008).*
Priyanka; Asian J Pharm Clin Res, Feb. 2019,12, 411-417. (Year: 2019).*
Schafer; Cellular Signalling 2014, 26, 2016-2029. (Year: 2014).*
Weber; Cancer Control, 2003, 10, 375-383. (Year: 2003).*
Waghule; Biomedicine and Pharmacotherapy 2019, 109, 1249-1258. (Year: 2019).*
Written Opinion of the International Search Authority in International Application PCT/US2020/029159, dated Oct. 29, 2020, 8 Pages. (Year: 2020).*
Eriksson; Journal of Pharmacy and Pharmacology, 2000, 52, 807-817. (Year: 2000).*
Gu; Molecular Pain 2010, 6, 64, 10 pages. (Year: 2010).*
Kelleher, ChemioCare launches development of transdermal patch for multiple myeloma drug—lenalidomide. Proactive Investors. Apr. 23, 2019. 2 pages. Accessible at .proactiveinvestors.com/companies/news/218960/chemiocare-launches-development-of-transdermal-patch-for-multiple-myeloma-drug—lenalidomide-218960.html.
Mandac et al., Lenalidomide induced good clinical response in a patient with multiple relapsed and refractory Hodgkin's lymphoma. J Hematol Oncol. May 28, 2010;3:20(1-3).
Pereira et al., Evaluation of the effects of thalidomide-loaded biodegradable devices in solid Ehrlich tumor. Biomed Pharmacother. Mar. 2013;67(2):129-32, Epub Sep. 18, 2012.

* cited by examiner

CONTINUOUS DELIVERY OF LENALIDOMIDE AND OTHER IMMUNOMODULATORY AGENTS

CROSS-REFERENCE TO RELATED APPLICATIONS

This application is a U.S. Non-Provisional Application which claims the benefit of priority to U.S. Provisional Patent Application No. 62/945,028, filed Dec. 6, 2019, and U.S. Provisional Patent Application No. 62/837,057 filed Apr. 22, 2019, each of which is hereby incorporated by reference in its entirety.

TECHNICAL FIELD

The present subject matter generally relates to a method comprising continuous delivery of immunomodulatory agents to a subject in need thereof. More particularly, embodiments relate to a continuous delivery of Immunomodulatory imide compounds at predetermined hourly dose of the drug for a predetermined number of days. Surprisingly, this method of continuous delivery improved anticancer activity or anti-inflammatory activity of the drug with reduced toxicities (such as neutropenia) when compared with a standard pulsatile dosing regimen.

BACKGROUND

Immunomodulatory imide compounds include thalidomide and thalidomide analogues (collectively the thalidomide family of compounds), which possess pleiotropic anti-myeloma properties including immune-modulation, anti-angiogenic, anti-inflammatory and anti-proliferative effects. The thalidomide analogues include lenalidomide, pomalidomide, iberdomide, and apremilast.

Lenalidomide (3-(4-amino-1-3-dihydro-1-oxo-2H-isoindol-2yl)-2,6-piperidinedione), as shown in Formula I below, is an FDA approved drug which is available in the form of an oral capsule. Lenalidomide is indicated, for example, for treatment of patients with multiple myeloma (MM) in combination with dexamethasone, MM as maintenance following autologous hematopoietic stem cell transplantation (auto-HSCT), transfusion-dependent anemia due to low- or intermediate-1-risk myelodysplastic syndromes (MDS) associated with a deletion 5q abnormality with or without additional cytogenetic abnormalities, mantle cell lymphoma (MCL) whose disease has relapsed or progressed after two prior therapies, one of which included bortezomib, previously treated follicular lymphoma (FL) in combination with a rituximab product, or previously treated marginal zone lymphoma (MZL) in combination with a rituximab product. Lenalidomide is available in an oral dosing form in strengths of 2.5 mg, 5 mg, 10 mg, 15 mg, 20 mg, and 25 mg.

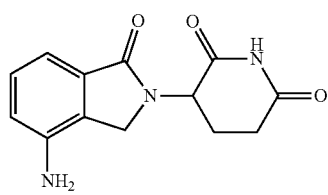

Formula I

Pomalidomide (4-amino-2-(2,6-dioxopiperidin-3-yl) isoindoline-1,3-dione), shown as Formula II below, is also a FDA approved drug, which is available in the form of oral capsules. Pomalidomide, is typically used, often in combination with dexamethasone, for patients with multiple myeloma who have received prior therapy (such as lenalidomide) and have demonstrated disease progression upon completion (or shortly thereafter) of the last therapy. Pomalidomide is available in an oral dosage form at strengths of 1 mg, 2 mg, 3 mg, and 4 mg.

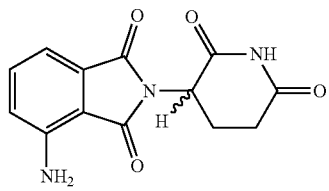

Formula II

Thalidomide (2-(2,6-dioxopiperidin-3-yl)isoindole-1,3-dione) shown as Formula III below, is a FDA approved drug, which is available in the form of oral capsules. Thalidomide, is typically used, often in combination with dexamethasone, for the treatment of patients with newly diagnosed multiple myeloma. Thalidomide is available in an oral dosage form at strengths of 50 mg, 100 mg, 150 mg, and 200 mg.

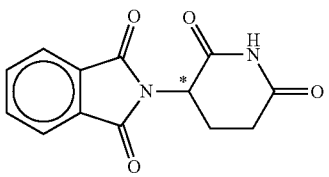

Formula III

Apremilast (N-[2-[(1S)-1-(3-ethoxy-4-methoxyphenyl)-2-(methylsulfonyl)ethyl]-2,3-dihydro-1,3-dioxo-1H-isoindol-4-yl]acetamide) shown as Formula IV below, is a FDA approved drug, which is available in the form of tablets. Apremilast is indicated for the treatment of patients with active psoriatic arthritis. Apremilast is available in an oral dosage form at strengths of 10, mg, 20 mg, and 30 mg.

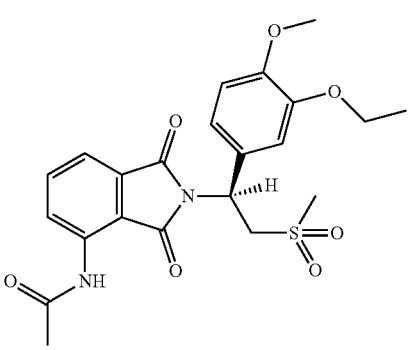

Formula IV

Iberdomide ((3S)-3-[7-[[4-(morpholin-4-ylmethyl)phenyl]methoxy]-3-oxo-1H-isoindol-2-yl]piperidine-2,6-dione), which is shown below as Formula V, is under development for treating refractory multiple myeloma.

Formula V

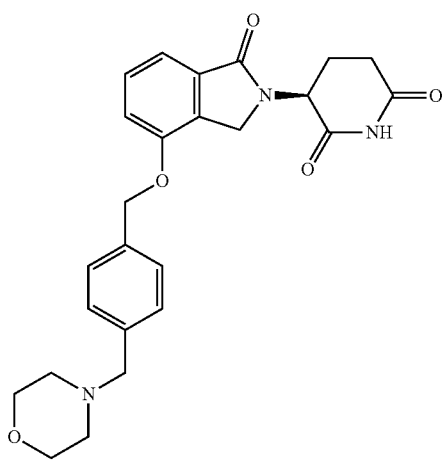

BRIEF SUMMARY

In a first aspect, a method of providing continuous administration of an immunomodulatory imide compound to a subject in need thereof is provided. The immunomodulatory imide compound is selected from the group of thalidomide or analogues thereof. Analogues of thalidomide include lenalidomide, pomalidomide, apremilast, and iberdomide. Other analogues of thalidomide may be selected from metabolites of thalidomide or its analogues, N-substituted analogues or tetrafluorinated analogues.

According to certain embodiments, the immunomodulatory agent is selected from the group consisting of thalidiomode and analogues of thalidomide, such as lenalidomide, pomalidomide, apremilast, and iberdomide. In some embodiments, the compound lenalidomide is selected from the group consisting of a lenalidomide base, lenalidomide cocrystals, lenalidomide in amorphous form, lenalidomide in a dehydrate form, lenalidomide in coated form, lenalidomide in solution form, lenalidomide in crystalline form as a specified polymorph or combination of polymorphs, lenalidomide salts, lenalidomide isomers (including the racemate, and individual enantiomer thereof), lenalidomide in solid solution, lenalidomide prodrugs, lenalidomide analogs, lenalidomide derivatives, lenalidomide metabolites, and combinations thereof. In further embodiments, the compound pomalidomide is selected from the group consisting of a pomalidomide base, pomalidomide cocrystals, pomalidomide in amorphous form, pomalidomide in coated form, pomalidomide in solution form, pomalidomide in crystalline form as a specified polymorph or combination of polymorphs, pomalidomide solvates, pomalidomide salts, pomalidomide isomers (including the racemate, and individual enantiomer thereof), pomalidomide in solid solution, pomalidomide prodrugs, pomalidomide analogs, pomalidomide derivatives, pomalidomide metabolites, and combinations thereof. In further embodiments, the compound thalidomide is selected from the group consisting of a thalidomide base, thalidomide cocrystals, thalidomide in amorphous form, thalidomide in coated form, thalidomide in solution form, thalidomide in crystalline form as a specified polymorph or combination of polymorphs, thalidomide solvates, thalidomide salts, thalidomide isomers (including the racemate, and individual enantiomer thereof), thalidomide in solid solution, thalidomide prodrugs, thalidomide analogs, thalidomide derivatives, thalidomide metabolites, and combinations thereof. In further embodiments, the compound apremilast is selected from the group consisting of the racemate of apremilast, the R isomer of apremilast, apremilast base, apremilast cocrystals, apremilast in amorphous form, apremilast in coated form, apremilast in solution form, apremilast in crystalline form as a specified polymorph or combination of polymorphs, apremilast solvates, apremilast salts, apremilast in solid solution, apremilast prodrugs, apremilast analogs, apremilast derivatives, apremilast metabolites, and combinations thereof. In further embodiments, the compound iberdomide is selected from the group consisting of the racemate of iberdomide, the R isomer of iberdomide, iberdomide base, iberdomide cocrystals, iberdomide in amorphous form, iberdomide in coated form, iberdomide in solution form, iberdomide in crystalline form as a specified polymorph or combination of polymorphs, iberdomide solvates, iberdomide salts, iberdomide in solid solution, iberdomide prodrugs, iberdomide analogs, iberdomide derivatives, iberdomide metabolites, and combinations thereof. In yet further embodiments, the immunomodulatory imide compound is present in the range of 0.01%-95% w/w of the total weight of the formulation.

According to embodiments provided herein, a continuous delivery platform comprises a formulation selected from the group consisting of a liquid formulation, a solid formulation, a semi-solid formulation, an emulsion formulation, a nanoparticle formulation, a matrix formulation, a film formulation, a patch formulation, and or combinations thereof. The embodiments are intended to be formulated to provide a continuous, sustained delivery to mitigate the peak and valley pharmacokinetic behavior associated with standard immediate release oral delivery forms. The embodiments are intended to be formulated to provide a route of administration selected from the group consisting of an oral, buccal, mucosal, rectal, transdermal, topical, parenteral, and or implantable, and or combinations thereof.

In liquid embodiments, the formulation is selected from the group consisting of solutions, dispersions, suspensions, emulsions which includes micro-emulsions, nano-emulsions, self-emulsifying, depot preparations, or micelles.

In solid embodiments, the formulation is selected from the group consisting of a capsule, tablet, sphere, solid dispersion, coated preparation, microsphere, nanosphere, particulate, micro-particulate, nano-particulate, sachet, powder, hot melt, extrusion, spray-dried preparation, depot preparations, micronization, wafer, or granulation.

In semisolid embodiments, the formulation is selected from the group consisting of oil-in-water and or water-in-oil emulsions, ointments, balms, creams, suppositories, gels, blends, or polymer solutions.

In matrix embodiments, the formulation is selected from the group consisting of a patch, wafer, or film.

In film embodiments, the formulation is selected from the group consisting of a dissolvable strip, dispersible strip or patch.

In implantable embodiments, the formulation is selected from the group consisting of a hot melt, water borne polymer composition, solvent borne polymer composition, depot preparations, absorbable polymer compositions, or biodegradable polymer compositions.

In transdermal embodiments, the formulation is selected from the group consisting of a reservoir patch, a micro-reservoir patch, a matrix patch, micro-needles, micro-protrusions, micro-blades, a drug-in-adhesive patch, a multi-layer patch, and an extended or sustained release film.

In any of the listed embodiments, the platform may be selected from any of the listed embodiments or combinations thereof.

Also provided is a method of treating diseases or conditions which the immunomodulatory imide compounds as disclosed herein were known to be capable of treating, including, for example, multiple myeloma, transfusion-dependent anemia due to low- or intermediate-1-risk myelodysplastic syndromes, mantle cell lymphoma, chronic lymphocytic leukemia, hematologic cancers, or solid tumor cancers, psoriatic arthritis, or cytokine release syndrome, wherein the method comprises continuous administration of the immunomodulatory imide compound to a subject in need of the treatment. In some embodiments, the method comprises administering the immunomodulatory imide compound continuously to a subject at a predetermined hourly rate for a predetermined number of days.

The immunomodulatory imide compound is administered in the form of a formulation comprising the immunomodulatory imide compound and a pharmaceutically acceptable carrier.

DETAILED DESCRIPTION

Figure 1:
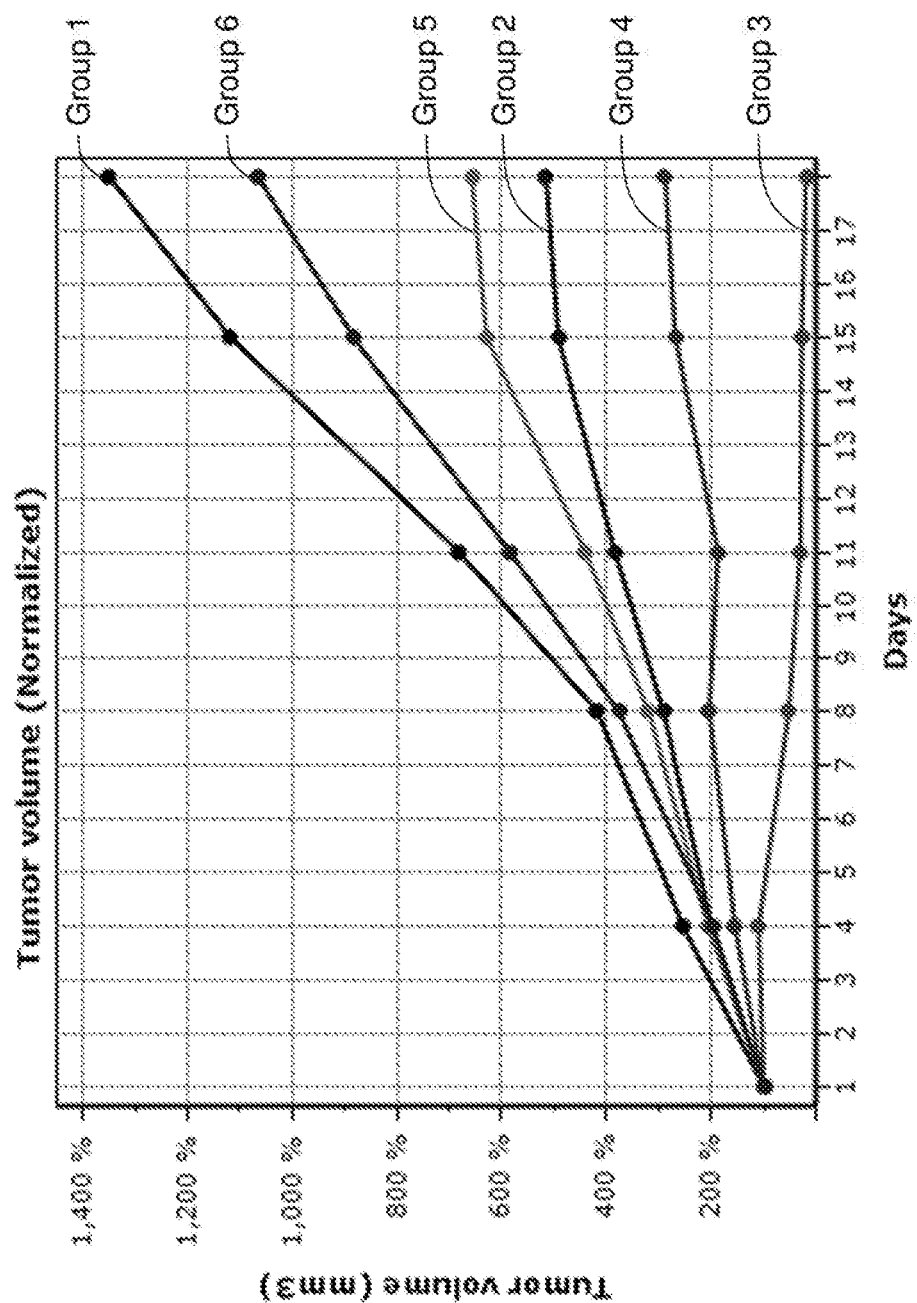
FIG. 1 demonstrates the tumor volume as a function of time, in days post continuous administration of lenalidomide at a various hourly rate (μg/h) comparing with a vehicle and intraperitoneal injection of lenalidomide once a day.

As used herein, the term "pharmaceutically acceptable salts" includes acid addition salts or addition salts of free bases. The term "pharmaceutically acceptable salts" within its scope include each of all the possible isomers and their mixtures, and any pharmaceutically acceptable metabolite, bioprecursor and/or pro-drug, such as, for example, a compound which has a structural formula different from the one of the compounds recited or described, yet is directly or indirectly converted in vivo into such a compound upon administration to a subject, such as a mammal, and particularly a human being.

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the term "active", "agent", or "therapeutic agent" refers to any molecule, compound, methodology and/or substance that is used for the prevention, treatment, management and/or diagnosis of a disease, disorder or condition.

As used herein, the term "effective amount" refers to the amount of a therapy or agent that is sufficient to result in the prevention of the development, recurrence, or onset of a disease or condition, the prevention, treatment, reduction or amelioration of one or more symptoms thereof, the enhancement or improvement of the prophylactic effect(s) of another therapy, the reduction of the severity or the duration of a disease or condition, the amelioration of one or more symptoms of a disease or condition, the prevention of the advancement of a disease or condition, the regression of a disease or condition or one or more of its symptoms, and/or the enhancement or improvement of the therapeutic effect(s) of another therapy.

As used herein, the phrase "pharmaceutically acceptable" means approved by a regulatory agency of the federal or a state government, or listed in the U.S. Pharmacopeia, European Pharmacopeia, Chinese Pharmacopeia, or other generally recognized pharmacopeia for use in animals, and more particularly, in humans.

As used herein, the term "treat", "treating", "treatment", or "therapy" of a disease or disorder refers to ameliorating the disease or disorder; for example slowing, arresting or reducing the disease, its development, or one or more clinical symptom thereof; the term also refers to alleviating or ameliorating one or more physical parameter, whether or not discernible by the patient; the term also refers to physically and/or physiologically modulating the disease or disorder (e.g. by stabilization of a discernible symptom and/or physical parameter).

As used herein, the term "prevention" of a disease or disorder refers to the administration of the compounds of the invention to a subject before any symptoms of that disease or disorder are apparent.

As used herein, a patient or subject is "in need of" a treatment if the patient or subject would benefit biologically, medically or in quality of life from such treatment.

The term "analog," "derivative" or "derivatized" as used herein includes chemical modification of a compound, or pharmaceutically acceptable salts thereof or mixtures thereof. That is, a "derivative" may be a functional equivalent of a compound which is capable of inducing the functional activity of the compound in a given subject or application.

As used herein, the terms "composition" and "formulation" may be used interchangeably, unless otherwise indicated. Generally, a formulation may be used as a stand-alone non-occlusive transdermal composition for application to the skin, or may be used in form of or to prepare a transdermal patch for application to the skin (patch formulation).

As used herein, the term "transdermal delivery" means delivery of drug into systemic circulation through the skin, which includes occlusive and non-occlusive delivery by a transdermal composition or a patch.

As used herein, the term "topical delivery" means delivery of a drug not into the systemic circulation through the skin, which includes occlusive and non-occlusive delivery by a topical composition or a patch.

As used herein, the term "a," "an," "the" and similar terms used in the context of the present invention are to be construed to cover both the singular and plural unless otherwise indicated herein or clearly contradicted by the context. The use of any and all examples, or exemplary language (e.g. "such as", "for example", "illustrative", "e.g.") provided herein is intended merely to better illustrate the invention and is not intended to limit the scope of the invention.

As used herein, the term "continuous delivery," "continuously administering," or "continuous administration" refers to essentially uninterrupted administration to a subject of a medication or drug. The administration is non-stop (uninterrupted) except when it is necessary to refill the medication or drug supply or to administer the next dose in the regimen. "Continuous delivery" means there is an uninterrupted administration of the medication or drug, and that the dosing rate or absorbance rate may fluctuate over the dosing interval.

As used herein, the term "therapeutic agent" refers to any molecule, compound, and/or substance that is used for the purpose of treating and/or managing a disease or disorder.

As used herein, the terms "therapies" and "therapy" can refer to any method(s), composition(s), and/or agent(s) that can be used in the prevention, treatment and/or management of a disease or condition, or one or more symptoms thereof. In certain embodiments, the terms "therapy" and "therapies" refer to small molecule therapy.

In an aspect, a method of providing continuous delivery of a therapeutically effective amount of a pharmaceutical composition or formulation comprising lenalidomide is provided. In some embodiments, the method delivers lenalidomide continuously at a predetermined hourly rate. In some embodiments, the predetermined hourly rate may range from 16 to 1400 µg/hour for example from 30 µg to 750 µg/hour, from 30 µg to 145 µg/hour, from 70 µg to 285 µg/hour, or from 185 µg to 725 µg/hour, such as 35 µg/hour, 75 µg/hour, 90 µg/hour, 140 µg/hour, 180 µg/hour, 190 µg/hour, 275 µg/hour, 450 µg/hour, or 700 µg/hour, or is an hourly rate between any two of these recited rates (inclusive), e.g., between 35-140 µg/hour or 75-280 µg/hour or 190 to 700 µg/hour.

In some embodiments, the method delivers lenalidomide continuously to achieve a steady state plasma level of the immunomodulatory imide compound in a range of 3-140 µg/L, such as 3.5-140 µg/L, 3-75 µg/L, 3.5-75 µg/L, 3.5-14 µg/L, 7.5-28 µg/L, 19-70 µg/L, 9 µg/L, 18 µg/L, or 45 µg/L.

In some embodiments, the method delivers the immunomodulatory imide compound continuously for a predetermined number of days. In some embodiments, the predetermined number of days is one day, two days, three days, four days, five days, six days, seven days, eight days, nine days, ten day, eleven days, twelve day, thirteen days, or fourteen days. In other embodiments, the predetermined number of days is between 1-14 days, 1-12 days, 1-10 days, 1-7 days, 1-5 days, 1-3 days, 2-14 days, 2-12 days, 2-10 days, 2-7 days, 2-5 days, 2-3 days, 3-14 days, 3-12 days, 3-10 days, 3-7 days, 3-5 days, 4-14 days, 4-10 days, 7-14 days or 7-10 days.

In some embodiments, the hourly rate is selected to achieve a plasma concentration comparable to the immunomodulatory imide compound plasma concentration provided by an oral dose between 0 to 24 hours, such as from about 1 to 24 hrs, further such as between about 5 and 24 hrs, and even further such as between about 5 hours and 23 hours or between about 10 hours and 16 hours after ingestion. The oral dose can be from 2.5 to 50 mg once daily, for example, 2.5 mg, 4.0 mg, 5 mg, 10 mg, 15 mg, 20 mg, 25 mg, 30 mg, or 50 mg of the immunomodulatory imide compound once daily or once every two days. The phrase "comparable to plasma concentration of an oral dose between 0 and 24 hours" can be understood from the description of Examples 6-9. For example, the area of the time concentration curve (AUC) calculated by the trapezoidal rule for the interval 0-24 hours from a graph of plasma concentration versus time of an oral dose divided by the hours (24 hours) is the hourly blood concentration associated with the AUC. The hourly AUC that can be achieved by the hourly rate of the continuous delivery method described herein would produce similar drug exposure over time exhibited by the oral dose. Such hourly rate of the continuous delivery method described herein is the one which achieves a plasma concentration comparable to the 0 hour to 24 hours blood level of an oral dose. In another embodiment, the continuous delivery method described herein achieves an AUC comparable to the AUC from an oral dose of the same compound in the 0-24 hour post dosing period.

In some embodiments, the method delivers the immunomodulatory imide compound continuously in a manner where the AUC thereof is between 10-60% of the exposure obtained from a standard of care treatment. The standard of care treatment can be intraperitoneal injection of, for example, 500 mcg once per day, or can be from 2.5 to 50 mg oral once daily, such as 2.5 mg, 4.0 mg, 5 mg, 10 mg, 15 mg, 20 mg, 25 mg, 30 mg, or 50 mg of the immunomodulatory imide compound once daily or once every two days via oral administration. In another embodiment, the method herein provides for continuous administration of the lenalidomide to provide an AUC that is between about 10 and 60% of the AUC provided by a standard of care treatment. In some embodiments, the standard of care treatment is an oral dose of lenalidomide from 2.5 mg to 50 mg once daily, such as at 2.5 mg, 5 mg, 10 mg, 15 mg, 20 mg, or 25 mg or 50 mg once daily or once every two days.

In some embodiments, the method delivers the immunomodulatory imide compound (such as lenalidomide) continuously at a dose rate that provides a blood level (µg/L) equivalent to the blood level at a time point from 10 hours to 16 hours obtained from daily oral dose of 2.5-50 mg once daily (e.g., 2.5 mg, 5 mg, 10 mg, or 25 mg of lenalidomide once per day). In the most preferred embodiments, the method delivers the immunomodulatory imide compound continuously at a dose rate that provides a blood level equivalent to the blood level at 12 hours obtained from daily oral dose of 2.5 to 50 mg once daily (e.g. 5 mg, 10 mg, or 25 mg of lenalidomide once per day). In some embodiments, the method is for treating newly diagnosed multiple myeloma and the daily oral dose of lenalidomide is 25 mg. In some embodiments, the method is for maintenance treatment of multiple myeloma and the daily oral dose of lenalidomide is 10 mg. In some embodiments, the method is for treating chronic lymphocytic leukemia and the daily oral dose of lenalidomide is 5 mg.

In some embodiments, the method delivers the immunomodulatory imide compound (such as lenalidomide) continuously at a dose rate such that the daily dose of the method is 10-75%, such as 15-70%, 15-25%, 40-50%, 10-45%, 45%-70%, 60-70%, 15%, 16%, 17%, 18%, 19%, 20%, 21%, 22%, 23%, 24%, 25%, 26%, 27%, 28%, 29%, 30%, 40%, 41%, 42%, 43%, 44%, 45%, 46%, 47%, 48%, 49%, 50%, 60%, 61%, 62%, 63%, 64%, 65%, 66%, 67%, 68%, 69%, or 70% of the daily dose of a standard of care treatment. In some embodiments, the standard of care treatment is intraperitoneal injection of, for example, 500 mcg once daily. In some embodiments, the standard of care treatment is FDA-approved once daily oral dose of the immunomodulatory imide compound such as at 5 mg, 10 mg, or 25 mg of lenalidomide oral once per day.

In various embodiments, the method may be used to treat multiple myeloma, transfusion-dependent anemia due to low- or intermediate-1-risk myelodysplastic syndromes, mantle cell lymphoma, solid tumor cancers, and hematological cancers. The thalidomide compound may be dissolved, suspended, dispersed, or uniformly mixed with a pharmaceutically acceptable carrier or combination of carriers for continuous delivery.

All pharmaceutically acceptable forms of immunomodulatory imide compound, such as thalidomide, analogs of thalidomide including lenalidomide, pomalidomide, apremilast, and iberdomide including, for example, free base, salts, polymorphs, solvates, solutions, isomers, amorphous, crystalline, co crystalline, solid solution, prodrugs, analogs, derivatives, and metabolites are contemplated for use in the methods described herein. The compound may be in the form of a pharmaceutically acceptable salt, such as an acid addition salt or a base salt, or a solvate thereof, including a hydrate thereof. Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

The formulation for continuous delivery of the immunomodulatory imide compound comprises the immunomodulatory imide compound and a pharmaceutically acceptable carrier. The pharmaceutically acceptable carrier should be compatible with other ingredients of the formulation, if any, and not harmful for the subject's health. Where the continuous delivery comprise infusion, the formulation ingredients may be selected to facilitate the infusion of the formulation. Exemplary carriers for formulations for continuous delivery include, without limitation, water, carboxymethyl cellulose (CMC), Tween 80, dimethyl sulfoxide (DMSO), ethanol, 2-hydroxypropyl-β-cyclodextrin, dextrose, and PEG400. When the formulation is in a liquid format, the immunomodulatory imide compound is present, in some embodiments, at a concentration of between about 0.01-20 mg/mL, 0.05-5 mg/mL, 0.05-3 mg/mL, 0.1-4 mg/mL, 0.1-2.0 mg/mL or between about 0.1-1 mg/mL.

The continuous delivery of the immunomodulatory imide compound in the form of a formulation can be achieved through infusion therapy via, for example, intravenous or subcutaneous application. Infusion therapy administers medication through the use of a sterile thin tube such as catheter that is inserted into the body and secured. A pump delivery system and any other delivery system that would deliver a continuous infusion such as depot injection and ambulatory pumps can be used for this purpose.

In some embodiments, lenamide is continuously delivered at a rate of 38-700 μg/hour. In some embodiments, the immunomodulatory imide compound is continuously delivered for at least one day, at least two days, at least three days, or at least four days. In some embodiments, lenamide is continuously delivered for at least 14 days. In some embodiments, lenamideis continuously delivered for 14 days, and after one day off the treatment with the immunomodulatory agent, lenamide is continuously delivered in 14-day cycles until disease progression or as a maintenance treatment provided continuously to prevent disease recurrence.

One study as described in Example 1 demonstrated that administration route has a role in the anti-cancer activity of the thalidomide compound. In this study, a composition comprising lenalidomide was continuously delivered via subcutaneous infusion or was delivered once a day via intraperitoneal injection to SCID mice wherein the mice were implanted with a H929 multiple myeloma xenograft. This study unexpectedly showed that the continuous infusion route effectively reduced the tumor size in all animals treated at 6 mcg/hr while the intraperitoneal injection at a higher dose slowed progression but did not inhibit the growth of the tumor size. See FIG. 1. This study also showed that the continuous infusion route did not result in substantial loss of body weight or hematologic toxicity. See FIG. 2 and Table 1.

In the study described in Example 1, the SCID mice in Group 2 were given the standard of care treatment which is a daily intraperitoneal dose of 25 mg/kg (500 mcg for 20 gm mouse) administered once a day. The pharmacokinetic profile of Group 2 displayed blood level Cmax of 2.9 mcg/mL at 0.08 hours and 0.013 mcg/mL at 18 hours. Further data demonstrated continuous blood levels of greater than those observed at 8 hours or 0.29 mcg/mL and lower than those observed at 18 hours or 0.013 mcg/mL were either toxic or ineffective. For example, if the continuous blood level is greater than that observed at 16 hours but less than that observed at 10 hours in daily intraperitoneal dose of 500 mcg administered once a day, it is effective and non-toxic. The maintenance of continuous dose specific blood levels in terms of their time range are predicted to be safe and effective and result in activity in humans.

The continuous delivery of the thalidomide compound can also be achieved through a transdermal delivery system. The continuous infusion model described above is used to emulate the application of a transdermal drug delivery. Both continuous infusion and transdermal delivery bypasses the first pass metabolic extraction, which can be observed with oral drug delivery. The blood level targets observed in a continuous infusion delivery are equivalent to those, which are produced by a transdermal patch. Transdermal patch drug delivery can be quantitated in terms of unit of drug (dose) per unit of time (hour). This delivery rate is then adjusted by the surface area of the transdermal patch to deliver an adequate amount of drug to achieve a specific blood level of drug. This specific blood level, in this embodiment, is the target level which was observed to be effective as a continuous infusion.

Lenalidomide is administered in an Immediate Release (IR) dosage form (tablet) which does not consider the need for a reduced onset or lower therapeutic window. In general, the intent of an IR tablet is to provide sufficient drug to obtain a therapeutic level in a therapeutic window for some period after initial absorption. In consideration of this therapeutic window, between 10 and 24 hours, the reduced onset refers to the initial absorption of the drug for up to about 10 hours where the maximum blood level is observed between 0.5 to 3 hours post-dose from the IR tablet. The therapeutic window for efficacious dose is considered between about 10 hours to about 24 hours. Thereby, as disclosed herein, the maximum observed blood level would not exceed the upper level of the therapeutic window for a given dose. By reducing the dose further, an IR tablet regimen to effectively reduce the potential for toxicity, the actual dose obtained in the therapeutic window between 10 and 24 hours is likely not achieved and this suggests efficacy from the current standard of care treatment, IR tablet, is not probable. The embodiments described herein provide for an increasing slow drug release and delivery up to the therapeutic window without significantly exceeding the therapeutic blood levels within the therapeutic window.

According to the present disclosure, the inventors have found that lenalidomide may be administered to the human body via a reduced and controlled and sustained method of delivery such as but not limited to: parenteral, infusion, subcutaneous, oral, mucosal, buccal, topical or transdermal application for the purpose of treating for example multiple myeloma and other diseases indicated for lenalidomide if administered in an amount effective to achieve substantially zero-order kinetics for the period of time of the duration of delivery. The method of delivery would provide a steady state release of lenalidomide via stated routes of administration. A delivery rate of about 16 µg/hour to about 1400µ/hour of lenalidomide, and more preferably about 38 µg/hour to about 700 µg/hour is needed to achieve a therapeutically effective dose in a patient. The current administration of lenalidomide is provided orally from about 2.5 to 25 mg per day with limited consideration given to the actual therapeutic efficacy window between about 1 to 24 hours.

Examples 6 and 7 exemplify the dose ranges of continuously administered lenalidomide predicted to be at a biologically equivalent dose to once oral daily lenalidomide at 25 mg a day (treating newly diagnosed multiple myeloma). Lenalidomide can be continuously administered at a dose equivalent to the blood level at a time point from 10 hours to 16 hours obtained from once daily lenalidomide at 25 mg a day. For example, the lenalidomide can be continuously administered at a dose providing blood level equivalent to the blood level at 12 hours obtained from once daily lenalidomide at 25 mg a day.

Example 8 exemplifies the dose ranges of continuously administered lenalidomide predicted to be at a biologically equivalent dose to once oral daily lenalidomide at 10 mg a day (multiple myeloma maintenance treatment). Lenalidomide can be continuously administered at a dose equivalent to the blood level at a time point from 10 hours to 16 hours obtained from once daily lenalidomide at 10 mg a day. For example, the lenalidomide can be continuously administered at a dose providing blood level equivalent to the blood level at 12 hours obtained from once daily lenalidomide at 10 mg a day.

Example 9 exemplifies the dose ranges of continuously administered lenalidomide predicted to be at a biologically equivalent dose to once oral daily lenalidomide at 5 mg a day (treating chronic lymphocytic leukemia). Lenalidomide can be continuously administered at a dose equivalent to the blood level at a time point from 10 hours to 16 hours obtained from once daily lenalidomide at 5 mg a day. For example, the lenalidomide can be continuously administered at a dose providing blood level equivalent to the blood level at 12 hours obtained from once daily lenalidomide at 5 mg a day.

Examples 6-9 used lenalidomide as an example to determine the hourly delivery rate and steady state plasma concentration of lenalidomide to be achieved for continuous administration of lenalidomide based on the PK profile of oral dose of lenalidomide. The hourly delivery rate and steady state plasma concentration of other immunomodulatory imide compounds for continuous administration of other immunomodulatory imide compounds can be similarly determined based on the PK profile of the corresponding immunomodulatory imide compound.

In one embodiment, a method for continuous delivery of an immunomodulatory imide compound comprises providing and/or applying a transdermal drug delivery system or a topical formulation comprising the immunomodulatory imide compound, and methods of use of the same, to provide a sustained drug plasma concentration of the immunomodulatory imide compound at a predetermined level for a predetermined period of time. In further embodiments, provided is a simplified and improved therapeutic regimen by decreasing dosing frequency and maintaining blood serum levels within a predetermined range.

Transdermal delivery systems (TDS) described herein include transdermal formulations which may be in form of a liquid or semi-solid form of a desired degree of viscosity, for example, a solution, suspension, nano suspension, micro suspension, dispersion, emulsion, micro emulsion, nano emulsion, gel, ointment, cream, paste, lotion, mousse, or balm. Alternatively the transdermal formulation may form part of a TDS that comprises the transdermal formulation. Exemplary TDS include, without limitation, topical formulations (e.g. for occlusive or non-occlusive application to the skin or mucous membrane), gels, lotions, sprays, metered dose transdermal sprays, aerosols, suppositories, magma, transdermal patches, bilayer matrix patches, multilayer matrix patches, monolithic matrix patches with or without adhesive, drug-in-adhesive patches, matrix reservoir patches (with a separate matrix reservoir optionally surrounded by adhesive), microreservoir patches, hydrogel matrix patches, mucoadhesive patches, adhesive systems, transdermally applicable tape, microneedle systems, iontophoresis systems, or combinations thereof. In further embodiments, the formulations provided herein provide for stable formulations of the active components in the formulations. For example, the formulations are shelf stable and maintain at least 90% of their activity over a predetermined time period, when stored under standard ambient conditions. In further embodiments, the formulations are shelf stable for at least 3 months, 6 months, 9 months, or a year.

In embodiments, the transdermal system or topical formulation may be in form of a liquid or gel and may be incorporated in a transdermal patch. For example, without limitation, the transdermal formulation may include a polymer matrix, which may be adhesive or non-adhesive, e.g., without limitation a polyacrylic adhesive. Matrix patches include those with a single matrix layer, or multiple matrix layers.

Usage of the described transdermal and topical systems described here will have dosages that vary depending on the mode of administration, the particular condition to be treated and the effect desired. Dosage may be transdermal application once daily for 1 day, 2 days, 3, day, 4 days, 5, days, 6 days, 7 days, 8 days, 9 days, 10 days, 11 days, 12 days, 13 days, or 14 days, or longer. Alternatively, application may be several times a day for 1 day, 2 days, 3, day, 4 days, 5, days, 6 days, 7 days, 8 days, 9 days, 10 days, 11 days, 12 days, 13 days, or 14 days, or longer. Alternatively transdermal application may be once every day, every 2 days, every 3 days every 4 days, every 5 days, every 6 days, every 7 days, every 8 days, every 9 days, every 10 days, every 11 days, every 12 days, every 13 days, or every 14 days.

In some embodiments, the transdermal or topical formulations provide for a predetermined rate of delivery of the active components of the transdermal patch over a predetermined time period. In some embodiments, the predetermined time period is 24 hours, 48 hours, 72 hours, 96 hours, 120 hours, 144 hours, 7 days, 8 to 13 days, two weeks, or 15 days. In some further embodiments, the predetermined rate is an essentially constant rate with a coefficient of variation of less than about 90%, 85% or 80% over a predetermined time period.

In yet further embodiments, the transdermal or topical formulations provide a steady absorption rate of the thalidomide compound (and any other optional drug) by the patient over a predetermined time. In some embodiments, the predetermined time period is 24 hours, 48 hours, 72 hours, 96 hours, 120 hours, 144 hours, 7 days, 8 to 13 days, two weeks, or 15 days. In some further embodiments, the predetermined rate is a constant rate.

In yet further embodiments, the transdermal or topical formulations provide a range of predetermined blood serum levels of the active components of the transdermal patches in a patient over a predetermined time. In some embodiments, the predetermined time period is 24 hours, 48 hours, 72 hours, 96 hours, 120 hours, 144 hours, 7 days, 8 to 13 days, two weeks, or 15 days.

In yet further embodiments, the transdermal or topical formulations provide a plasma concentration of the active components of the transdermal patches in a therapeutic range in a patient over a predetermined time. In some embodiments, the predetermined time period is 24 hours, 48 hours, 72 hours, 96 hours, 120 hours, 144 hours, 7 days, 8 to 13 days, two weeks, or 15 days.

In yet further embodiments, the transdermal or topical formulations described herein allow for reduced variability in dosage of the active components in a patient over a predetermined time. In some embodiments, the predetermined time period is 24 hours, 48 hours, 72 hours, 96 hours, 120 hours, 144 hours, 7 days, 8 to 13 days, two weeks, or 15 days.

In some embodiments, the transdermal or topical formulation provided herein may be administered in dosage regimens such as once in a day, once in two days, once in three days, once in four days, once in five days, once in six days, once in a week, once in 8 to about 13 days, once in two weeks, once in 15 days to about 30 days.

In yet further embodiments, a pharmacokinetic assessment is performed on a blood sample of a subject who has been treated using the transdermal delivery systems described herein. The transdermal formulations are adjusted in response to the pharmacokinetic assessment. For example, the dosage may be adjusted such that a smaller patch, larger patch, or multiple transdermal patches are applied to the subject, or a patch having a more or less of a dose of active ingredients may be applied. In some embodiments, the formulation will be available in various dosage strengths and patch sizes in order to achieve optimum therapeutic outcome based on the subject's requirements. In one embodiment, more than one transdermal system or topical formulation is applied to a subject, and in some embodiments, between 1-5, 1-4, 1-3, 1-2, 2-5, 2-4, 2-3 patches are applied, and in other embodiments, 1, 2, 3, 4, 5, or 6 patches are applied.

Matrix-forming or gel-forming polymers may be used to form a transdermal gel, reservoir patch or matrix patch, and a large number of such polymers may be employed alone or in combination in amounts depending on the particular delivery vehicle and intended use (e.g. viscosity, duration of application, adherence etc.) as will be apparent to a person of ordinary skill. Exemplary polymers include, without limitation, cellulose and its derivatives (such as but not limited to hyrdroxy methyl cellulose, Aquasolve™ hypermellose acetate succinate, hydroxypropyl methyl cellulose, hydoxypropyl cellulose, ethyl cellulose, hydroxyethyl cellulose, methyl cellulose, carboxymethyl cellulose, sodium carboxymethyl cellulose, microcrystalline cellulose blends, cellulose acetate phthalate, propylmethylcellulose phthalate, etc.), biodegradable polymers (such as but not limited to gelatin, chitosan, starch, polyacrylic acid, polyvinyl, etc.), gums (such as but not limited to guar gum, gum copal, gellum gum, xanthan gum, locust bean gum, gum arabic, tragacanth, cassia gum, karaya gum etc.), polysaccharides (such as but not limited to carrageenan, agar, pectin, mannan, alginic acid, dextran, pullulan, etc.).

Adhesives polymers may be made from various materials which include plastics, polymers, pressure sensitive adhesives, self-adhering systems, or may require additional excipients to obtain pressure sensitive properties. Basic adhesive systems are selected from silicones, polyacrylics, polyisobutylenes, rubbers, and combinations thereof either by physical blending or copolymerization is disclosed. These materials may be obtained from solvent-borne, water-borne, physical mixtures, extruded, co-extruded, hot melt, or otherwise formed as polymerized or unpolymerized materials.

Suitable silicone adhesives include pressure sensitive adhesives made from silicone polymer and resin. The polymer to resin ratio can be varied to achieve different levels of tack. Specific examples of useful silicone adhesive which are commercially available include the standard BIOPSA® series (7-4400, 7-4500, and 7-600 series) and the amine compatible (endcapped) BIOPSA® series (7-4100, 7-4200, and 7-4300 series) manufactured by Dow Corning. Preferred adhesives include BIO-PSA® 7-4101, 7-4102, 7-4201, 7-4202, 7-4301, 7-4302, 7-4401, 7-4402, 7-4501, 7-4502, 7-4601, and 7-4602.

Suitable polyisobutylene adhesives are those which are pressure sensitive and have suitable tack. The polyisobutylene can comprise a mixture of high and medium molecular weight polyisobutylenes, polybutenes, and mineral oils. Specifically, high molecular weight polyisobutylenes are those with a molecular weight of at least about 425,000. Medium molecular weight polyisobutylenes are those with a molecular weight of at least 40,000 but less than about 425,000. Low molecular weight polyisobutylenes are those with a molecular weight of at least 100 but less than about 40,000. Specific examples of useful polyisobutylene adhesives which are commercially available include Oppanol® High Molecular Weight N grades 50, 50SF, 80, 100 and 150, and Oppanol® Medium Molecular Weight B grades 10N, 10SFN, 11SFN, 12SFN, 12N, 13SFN, 14SFN, 15SFN, and 15N manufactured by BASF. Specific examples of polybutenes are commercially available from Soltex as polybutenes of various molecular weights and by Ineos as Indopol and Panalane with various molecular weights. Specific example of useful polyisobutylene adhesives which is commercially available include Duro-Tak® 87-6908.

Useful acrylic polymers include various homopolymers, copolymers, terpolymers and the like of acrylic acids and derivatives thereof as a cross-linked, cross-linkable, uncross-linked, uncross-linkable, grafted, block, cured and non-curing pressure sensitive adhesives (PSAs). These acrylic polymers include copolymers of alkyl acrylates or methacrylates. Polyacrylates include acrylic acid, methacrylic acid, and deriviates thereof without limitation, methyl acylate, methyl methacrylate, ethyl acrylate, ethyl methacrylate, n-butyl acrylate, n-butyl methacrylate, hexyl acrylate, 2-ethylbutyl acrylate, isooctyl acrylate, 2-ethylhexyl acrylate, 2-ethylhexyl methacrylate, decyl acrylate, decylmethacrylate, dodecyl acrylate, dodecyl methacrylate, tridecyl acrylate, tridecyl methacrylate, vinyl acetate, 2-hydroxyethyl acrylate, glycidyl methacrylate, or octylacrylamide. The acrylic polymer may be functional species with levels of hydroxyl or carboxyl moieties or combinations thereof, non-functional species without functional moieties, non-reactive species with moieties which are less reactive than hydroxyl or carboxyl moieties, such as methyl or ethyl or propyl or butyl capped acrylamides. Exemplary acrylic PSA include, without limitation, one or more of: Duro-Tak® 87-900A, Duro-Tak® 87-9301, Duro-Tak® 87-4098, Gelva® GMS 3083, Gelva® GMS 3253, Duro-Tak® 387-2510/87-2510, Duro-Tak® 387-2287/87-2287, Duro-Tak® 87-4287, Gelva® GMS 788, Duro-Tak® 387-2516/87-2516, Duro-Tak® 87-2074, Duro-Tak® 87-235A, Duro-Tak 387-2353/87-2353, Gelva GMS 9073, Duro-Tak® 87-2852, Duro-Tak® 387-2051/87-2051, Duro-Tak® 387-2052/87-2052, Duro-Tak® 387-2054/87-2054, Duro-Tak® 87-2194, Duro-Tak ® 87-2196

Other pressure sensitive adhesives obtained from rubber block copolymers, such as Styrene-Isoprene-Styrene (SIS) or Styrene-Butadiene-Styrene (SBS, based adhesives are disclosed.

Film forming, rheological property modifying and or thickening polymers such as but not limited to starch and its derivatives, gelatin and its derivatives, polyvinyl alcohol and its derivatives, polyvinylpyrrolidone and its derivatives, ethylene and its derivatives, propylene and its derivatives, ethylene-vinyl acetate (EVA) and its derivatives. Film forming polymeric materials include methylcellulose and its derivatives, microcrystalline cellulose and its derivatives, cellulose and its derivatives, acrylates and copolymers thereof. Specific examples of these materials includes Kollidon® 12, 17, 30, 90 and VA64 from BASF. Additional examples include Elvanol from Kuraray. Pure-Cote®, Instant Pure-Cote®, Pure-Gel® and Pure-Dent® are various starch grades from Grain Processing Corporation. Specific examples of EVA include Ateva® Standard grades obtained from Celanese, ammonioalkyl methacrylate copolymers (e.g. EUDRAGIT® L100-55, EUDRAGIT® E PO, EUDRAGIT® RL, EUDRAGIT E® 100, PLASTOID® B, dimethylaminoethyl methacrylate-butyl methacrylate-methyl methacrylate copolymer).

In embodiments, the formulation may comprise one or more optional carriers and excipients, some of which may have dual or multiple functionality, e.g. a particular excipient may function as, e.g., a penetration enhancer or as, e.g., a plasticizer, or both, depending on concentration, type of transdermal system, and its components. Optional carriers or excipients include, without limitation, solvents, solubilizers, diluents, suspending agents, dispersing agents, gelling agents, polymers, biodegradable polymers, penetration enhancers, plasticizers, pH adjusting agents, buffering agents, pH stabilizers, emulsifying agents, auxiliary emulsifying agents, surfactants, suspending agents, stabilizers, preservatives, chelating agents, complexing agents, emollients, humectants, demulcents, skin irritation reducing agents, antioxidants, oxidants, tackifiers, fillers, volatile chemicals, and materials need to prepare a patch or film-like formulation.

In embodiments, the formulation may comprise a solvent, e.g. one or more of a C1-C20 alcohol (e.g., without limitation, one or more of: methanol, ethanol, isopropyl alcohol, butanol, propanol, 2-methyl-2-propanol, aka t-butyl alcohol, pentanol, 2,4-dimethyl-2-pentanol, 3,5-dimethyl-3-hexanol, and alcohols having C7, C8, C9, C10, C11, C12, C13, C14, C15, C16, C17, C18, C19 or C20 carbon atoms), polyhydric alcohols, glycols (e.g., without limitation: propylene glycol, polyethylene glycol, dipropylene glycol, hexylene glycol, butyene glycol, glycerine), derivatives of glycols, pyrrolidone (e.g., without limitation: N methyl 2-pyrrolidone, 2-pyrrolidone), sulfoxides (e.g., without limitation: dimethyl sulfoxide aka DMSO and decymethylsulfoxide), dimethyl-isosorbide, mineral oils, vegetable oils, water, polar solvents, semi polar solvents, non polar solvents, volatile chemicals which can be used to prepare patch formulations such as but not limited to esters, ketones, alcohols, alkanes, such as ethyl acetate, acetone, dichloromethane, chloroform, heptane, hexane, siloxanes, ethanol, isopropanol, toluene, and acids such as acetic acid, lactic acid, levulinic acid, and bases.

In embodiments, the formulation may comprise a surfactant, solubilizer, emulsifying agent, or dispersing agent, including anionic, cationic, nonionic and amphoteric surfactants, e.g. one or more of a propylene glycol, monocaprylate type I, propylene glycol monocaprylate type II, propylene glycol dicaprylate, medium chain triglycerides, propylene glycol monolaurate type II, linoleoyl polyoxyl-6 glycerides, oleoyl-polyoxyl-6-glycerides, lauroyl polyoxyl-6-gylcerides, polyglyceryl-3-dioleate, diethylene glycol monoethyl ether, propylene glycol monolaurate type I, polyglyceryl-3-dioleate, caprylocaproyl polyoxyl—8 glycerides, cyclodextrins, Diethylene glycol monoethyl ether (DEGEE), a polysorbate/polyethoxylated sorbitan ester or Tween®-type surfactant, a sorbitan ester or Span®-type solvent surfactant, a glycol, hexylengycol, a Brij® type surfactant, and sodium lauryl sulfate. DEGEE (also known as Di(ethylene glycol) ethyl ether or 2-(2-Ethoxyethoxy)ethanol)) is commercially available e.g. under the various trade names including Transcutol® (TC), Transcutol® P, Transcutol® CG, Transcutol® HP (Gattefosse, Lyon, France), and Carbitol™ (Dow Chemicals, Midland Mich.). The Span® or Tween® surfactant may, without limitation, be selected from one or more of: Span 20®, Span®40, Span® 60, Span®80, Span®83, Span®85, Span®120, Tween 20®, Tween 21®, Tween 40®, Tween 60®, Tween 61®, Tween 65®, and Tween 80®. Brij® is a group of nonionic surfactants commercially available from various sources (e.g. Sigma-Aldrich), and may be selected from one or more of Brij® 93 (average Mn ~357), Brij® S 100 (average Mn ~4,670), Brij® 58 (average Mn ~1124), Brij® O10 (average Mn ~709, also known as Brij 97, C18-1E10, Polyoxyethylene (10) oleyl ether, C18H35(OCH2CH2)nOH, n~10), Brij® C10 (average Mn ~683), Brij® L4 (average Mn ~362, also known as polyethylene glycol dodecyl ether, polyoxyethylene (4) lauryl ether, (C20H42O5)n), BRIJ® O20 (average Mn ~1,150, Polyoxyethylene (20) oleyl ether, C18H35 (OCH2CH2)nOH, n~20), Brij® S2 MBAL (also known as Brij® S2, polyethylene glycol octadecyl ether, polyoxyethylene (2) stearyl ether, main component: diethylene glycol octadecyl ether, C18H37(OCH2CH2)2OH), Brij® S10 (average Mn ~711), Brij® S20, and Brij® 35 (also known as Brij® L23, C12E23, polyoxyethylene lauryl ether, $(C_2H_4O)$ $nC_{12}H_{26}O$). Suitable amounts of a surfactant to include into formulations to perform a surfactant function may be from 0.01-95% w/w, less than 5% w/w typically e.g. less than 4, 3, 2, 1, or 0.5%. Suitable amounts for solvent/solubilizing functions may be from 5% to about 50%. Amounts may be increased or decreased to achieve a suitable and sufficient amount, as will be apparent to a person of ordinary skill in the art.

A glycol is class of small organic compounds (e.g. MW typically below 150 Daltons), or a polymer thereof, that belongs to the alcohol family, and wherein two hydroxyl (—OH) groups are attached to different carbon atoms. The simplest member of the glycol class is ethylene glycol (also known as 1,2-ethanediol), other members include, without limitation, propylene glycol (also called 1,2-propanediol), butylene glycol (1,3-butanediol), 1,4-butanediol, pentylene glycol, (1,2-pentanediol), hexylene glycol (2,4-pentanediol), 2-ethyl-1,3-hexanediol, and 2-methyl-2-propyl-1,3-propanediol. Similarly, higher molecular weight polymers of the above glycol diols, in particular of ethylene glycol, may be used; these include, without limitation, polyethyleneglycol (PEG). PEGs are available in different molecular weights, typically from about 200 g/mol to about 10,000,000 g/mol, e.g. PEG 200, 300, 400, 600, 800, 1000, 1500, 3350, 4000, 6000, 8000, 10,000, 20,000, 35,000. PEGs of different molecular weight have similar surfactant properties but the higher molecular weight polymers may be preferred for their additional thickening function which may be desired in some patch formulations.

A permeation enhancer may be included into a formulation for use in methods of the invention. Numerous penetration enhancers that include structurally diverse compounds are known and may be used alone or in combination, as will be apparent to a person of ordinary skill. For example, penetration enhancers may include one or more of alcohols (e.g. ethanol, propanol, isopropanol, nathanol, dodecanol, propylene gycol, gycerol), ethers alcohol such as but not limited to (diethylene glycol monoethyl ether), fatty acids, fatty alcohols, fatty acid derivatives, fatty alcohol derivatives, sulfoxides (e.g. dimethylsulfoxide, decylmethyl sulfoxide), amides (e.g. dimethylformamide, azone, urea, dimethylacetamide), pyrrolidone derivatives (e.g. 1-methyl-4-carboxy-2-pyrrolidone, 1-methyl-2-pyrrolidone, 1-lauryl-4-methoxycarbonyl-2- pyrrolidone), terpenes (e.g. menthol, limonene, terpineol, pinene, carvol), terpenoids, ethyl acetate, methyl acetate, octisalate, pentadecalactone, and acrylamide, triglycerides (e.g. triacetin), polyoxyethylene fatty alcohol ethers, polyoxyethylene fatty acid esters, esters of fatty alcohols, essential oils, surfactant type enhancers such as but not limited to (brij, sodium lauryl sulfate, tween, polysorbate). Other all penetration or permeation enhancers that may be included are those referred in the book "Percutaneous Penetration Enhancers" (Eric W. Smith, Howard I. Maibach, 2005. November, CRC press). In some embodiments, the permeation enhancer may be present in the range of 0.01% -95% w/w.

Fatty acid or alcohol permeation enhancers include those wherein the fatty acid, fatty acid derivative, fatty alcohol, or fatty alcohol derivative consists of a substituted fatty acid moiety, or a substituted fatty alcohol moiety, e.g., wherein the fatty acid moiety or the fatty alcohol moiety of the enhancer has a carbon chain length from C4 to C26. This may include, for example, without limitation, fatty acid esters, in particular those wherein the fatty acid or fatty acid part moiety has a carbon chain length of C4 to C26, or longer, including in particular C4, C5, C6, C7, C8, C10, C11, C12, C14, C16, C18, C20, C22, C24 and C26, or combinations thereof. For example, one or more of C12-26 fatty acids, alcohols and their derivatives, e.g. C18, may be combined with a shorter chain fatty acid from C4 to C10 (e.g., without limitation, C4, C5, C6, C7, C8, C10). Example derivatives include substituted fatty acids or fatty alcohols, for example as described herein, comprising one or more additional group selected from, without limitation, hydroxyl, ethyl, methyl, propyl, butyl, and glyceryl.

Exemplary particular fatty acid or alcohol permeation enhancers include, without limitation, saturated, unsaturated, monounsaturated and polyunsaturated fatty acids, e.g., without limitation, omega-3, omega-6, omega-7 and omega-9 fatty acids. The saturated, unsaturated, monounsaturated and polyunsaturated fatty acids may include, e.g., without limitation, fatty acids with a carbon chain of C12, C14, C16, C18, C20, C22, C24 and C26, in particular, without limitation, e.g. C14, C16, C18, and C20. Fatty acid or alcohol permeation enhancers further include, e.g., branched-chain saturated fatty acids, including, without limitation, methyl-branched fatty acids, e.g. isostearic acid, and ethyl-branched fatty acids. Fatty acid or alcohol permeation enhancers also include, e.g., one or more monounsaturated fatty acid, or a derivative thereof, including, without limitation, one or more of 5-dodecenoic acid (C12:1), 7-tetradecenoic acid (14:1), palmitoleic acid (16:1), oleic acid (C18:1), vaccenic acid (C18:1), elaidic acid (C18:1), paullinic acid (C20:1), gondoic acid (C20:1), erucic acid (C22:1), 15-docosenoic acid (C22:1), 17-tetracosenoic acid (24:1), nervonic acid (C24:1), and ximenic acid (C26:1), or one or more derivative thereof. Fatty acid or alcohol permeation enhancers further include, e.g., one or more of oleic acid ("OA", C18:1) and oleic acid derivatives. Oleic acid derivatives may include, e.g., one or more of ethyl oleate (OA ethyl ester), oleyl oleate (OA oleyl ester), glyceryl oleate (OA glyceryl ester), sorbitan monooleate (sorbitan oleate, Span® 80), and oleyl alcohol (cis-9-octadecen-1-ol). Fatty acid or alcohol permeation enhancers still further include, e.g., one or more of polyunsaturated fatty acid, and a polyunsaturated fatty acid derivative; and the polyunsaturated acids may include, without limitation, one or more of: hexadecatrienoic acid (16:3), linoleic acid (C18:2), rumenic acid (C18:2), alpha-linolenic acid (C18:3), gamma-linolenic acid (C18:3), calendic acid (C18:3), stearidonic acid (C18:4) mead acid (C20:3), eicosadienoic acid (C20:3), eicosatrienoic acid (C20:3), dihomo-gamma-linolenic acid (C20:3), arachidonic acid (C20:4), docosadienoic acid (C22:2), adrenic acid (C22:4), osbond acid (C22:5), tetracosatetraenoic acid (C24:4), tetracosapentaenoic acid (C24:5), and derivatives thereof, including without limitation, one or more of alcohols and esters, e.g. linoleyl alcohol (the fatty alcohol of linoleic acid). Fatty acid or alcohol permeation enhancers yet further include, e.g., one or more of saturated fatty acids, and saturated fatty acids derivatives; the saturated fatty acids may include, without limitation, one or more of: stearic acid (C18:0), palmitic acid (C16:0), myristic acid (C14:0), and lauric acid (C12:0). Fatty acid or alcohol permeation enhancers also include, e.g., one or more fatty acid ester, fatty acid ester derivative, and fatty acid derivative; these may include, without limitation, one or more of: ethyl oleate, methyl oleate, decyloleate, glyceryl monooleate, oleyl oleate, isopropyl palmitate (ester of isopropyl alcohol and palmitic acid), myristate, isopropyl myristate, methyl laurate (lauric acid methyl ester), glyceryl laurate (lauric acid glyceryl ester, monolaurin, glycerol monolaurate), lauryl laurate, propylene glycol monolaurate type I, propylene glycol monolaurate type II (e.g. lauroglycol™ 90, commercially available from Gattefosse, Lyon, France), lauryl lactate (ester of lauryl alcohol and lactic acid), and butyl acetate. Alternatively or additionally, the fatty acid or alcohol permeation enhancers may be provided in form of an oil, or an enriched part/fraction of an oil, e.g. a plant-derived oil, that is rich in one or more fatty acid or alcohol. For example, the oil may contain, without limitation, one or more fatty acid, monounsaturated fatty acid, and polyunsaturated fatty acid. An enriched fraction of such an oil that contains fatty acid or alcohol of interest may be formed and used. Oils with suitable fatty acids include, without limitation, olive oil, macadamia oil, rapeseed oil, wall flower seed oil, mustard seed oil, nutmeg, palm oil, and coconut oil. Suitable oil fractions may include an "MCT oil" or "LCT" oil enriched e.g. in one or more of C8, C10, C12, C14, C16, C18 fatty acids.

Fatty alcohol permeation enhancers may include, without limitation, one or more saturated, monounsaturated or polyunsaturated fatty alcohol; which may include, without limitation, one or more of: butanol (C4), butyl alcohol (C4), tert-butyl alcohol (C4), tert-amyl alcohol (C5), 3-Methyl-3-pentanol (C6), capryl alcohol (C8), pelargonic alcohol (C9), capric alcohol (C10), Undecyl alcohol (C11), Lauryl alcohol (C12), Tridecyl alcohol (C13), Myristyl alcohol (C14), Pentadecyl alcohol (C15), Cetyl alcohol (C16), Palmitoleyl alcohol (cis-9-hexadecen-1-ol, C16H32O), Heptadecyl alcohol (1-n-heptadecanol, C17H36O), Stearyl alcohol (C18:0), Oleyl alcohol (C18H36O, C18:1), linoleyl alcohol (C18H34O, cis,cis-9,12-Octadecadien-1-ol), Nonadecyl alcohol (C19), Arachidyl alcohol (C20H42O), octyldodecanol (C20H42O, 2-Octyldodecan-1-ol), Heneicosyl alcohol (C21), Behenyl alcohol (C22H46O), Erucyl alcohol (cis-13-docosen-1-ol, C22H44O), Lignoceryl alcohol (C24), and Ceryl alcohol (C26). Saturated fatty alcohol permeation enhancers may include, without limitation, one or more of: lauryl alcohol (C12), isolauryl alcohol (C12, 10-methyl-1-hendecanol), anteisolauryl alcohol (C12, 9-methyl-1-hendecanol), myristyl alcohol (C14), isomyristyl alcohol (C14, 12-methyl-1-tridecanol), anteisomyristyl alcohol (C14, 11-methyl-1-tridecanol), cetyl alcohol (C16), isopalmityl alcohol (C16, 14-methyl-1-pentadecanol), anteisopalmityl alcohol (C16, 13-methyl-1-pentadecanol), stearyl alcohol (C18), isostearyl alcohol (C18, 16-methyl-1-heptadecanol), and anteisostearyl alcohol (C18, 15-methyl-1-pentadecanol).

Fatty alcohol or acid permeation enhancers with a longer carbon chain length may be preferred for their non-irritant or skin protective effect when present in formulations for use in the methods described herein; these include e.g., without limitation, C12-C26 fatty alcohols or acids as hereinabove described, preferably C12-C18 fatty alcohols or acids as hereinabove described, and may include saturated, monounsaturated or polyunsaturated alcohols or acids. These may be combined with shorter chain permeation enhancers wherein the fatty acid/alcohol or fatty acid/alcohol moiety has a carbon chain length of C4 to C10 (i.e. C4, C5, C6, C7, C8, C10, or combinations thereof); for example, one or more of butyric acid (C4:0), isobutyric acid (C4:0), valeric acid (C5:0), isovaleric acid (C5:0), levulinic acid (C5:0), caproic acid (C6:0), caprylic acid (C8:0), capric acid (C10:0), butanol, butyl alcohol, 2-butanol, isobutanol, tert-butanol. These shorter length fatty alcohol or acid permeation enhancers may preferably be included in a smaller amount than the longer ones, e.g. from about 1% to about 10% for the longer chain enhancers, and from about 0.1% to about 5% for the shorter chain enhancers, more preferably from about 0.5% to about 2%, e.g. from about 0.5% to about 1%.

Preferred fatty alcohol or acid permeation enhancers for the formulations described herein may include, without limitation, one or more of: oleic acid, ethyl oleate (OA ethyl ester), oleyl oleate (OA oleyl ester, C36H68O2), glyceryl oleate (OA glyceryl ester), decyl oleate, sorbitan monooleate (sorbitan oleate, Span 80), glycerol monooleate, and oleyl alcohol (cis-9-octadecen-1-ol), elaidic acid (C18:1), gondoic acid (C20:1), erucic acid (C22:1), nervonic acid (C24:1), and ximenic acid (C26:1), or one or more derivative thereof. Polyunsaturated acids such as hexadecatrienoic acid (16:3), linoleic acid (C18:2), alpha-linolenic acid (C18:3), gamma-linolenic acid (C18:3), calendic acid (C18:3), stearidonic acid (C18:4) mead acid (C20:3), eicosadienoic acid (C20:3), eicosatrienoic acid (C20:3), dihomo-gamma-linolenic acid (C20:3), arachidonic acid (C20:4), docosadienoic acid (C22:2), and derivatives thereof, including without limitation, alcohols and esters, e.g. linoleyl alcohol (the fatty alcohol of linoleic acid).

It is preferred that the permeation or penetration enhancer (or combination thereof) be non-irritating to human skin for the duration of use, or be used in an amount that is non-irritating for the duration of use, in particular when the use is in form of an in-adhesive patch over multiple days. Many known penetration enhancers are irritating to human skin, especially when used for a prolonged period and especially when used in form of an occlusive or semi-occlusive patch (rather than e.g. a topical application such as e.g. a lotion). As will be apparent to the skilled person that the amount of the optional penetration enhancer should be sufficiently low to avoid such irritation. In formulations according to the invention, it is preferred to exclude any skin-irritating penetration enhancers or other skin-irritating excipients, and if used, it is preferred to include them only in a low non-irritating amount.

The formulations described herein may comprise one or more plasticizer to avoid brittleness and impart flexibility to the adhesive matrix layer. The necessity and choice of plasticizer will depend on the particular adhesive and formulation. Suitable plasticizers are well known in the art. For example, without limitation, the one or more optional plasticizer may be selected from, without limitation, one or more of: glycols (in particular, without limitation, e.g. polyethylene glycol 400, polyethylene glycol 600, propylene glycol), higher alcohols (e.g. dodecanol), surfactants, sebacic acid esters (e.g. dibutyl sebacate, diethyl sebacate), citric acid esters (e.g. tributyl citrate, triethyl citrate), phthalic acid esters (e.g. diethyl phthalate, dibutyl phthalate), glycerol or glycerol esters (e.g. glycerine triacetate, glycerin), sugar alcohols (e.g. sorbitol, sucrose), tartaric acid esters (e.g. diethyl tartrate), oil (e.g. silicone oil, mineral oil), triacetin, oelic acid esters, adipate, and diisopropyl adipate. For inclusion into an adhesive patch formulation, and in particular an acrylic PSA patch formulation, preferred plasticizers include, without limitation, one or more of glycerol and glycerol esters. Further plasticizers may be found in "Handbook of Plasticizers" by George Wypych, 2004, Chem Tec Publishing), which is hereby incorporated by reference in its entirety. In certain embodiments, the plasticizers are present in the range of 0.01%-95% w/w.

Further optional excipients include for example, without limitation, one or more pH adjusting and buffering agents selected from, without limitation, buffers (e.g. citrate buffer, phosphate buffer, acetate buffer), acids and acid derivatives (e.g. carboxylic acid, organic acid, inorganic acid, sulfonic acid, halogenated carboxylic acids, vinylogous carboxylic acids, hydrochloric acid, acetic acid, succinic acid, citric acid, ascorbic acid, phosphoric acid), bases and base derivatives, e.g. sodium bicarbonate, sodium carbonate, trimethylamine, triethanolamine, sodium hydroxide, calcium hydroxide, potassium hydroxide, ammonium hydroxide, and tromethamine. Preferably, weak organic acids or weak organic bases are used as pH adjusting agents. The pH adjusting/buffering agent or stabilizer helps to maintain the appropriate pH of the transdermal formulation.

Still further optional excipients include for example, without limitation, one or more of emulsifying agents, auxiliary emulsifying agents, surfactants, suspending agents, preservatives, antioxidants, chelating agents, emollients, humectants, demulcents, skin irritation reducing agents, tackifiers, fillers, cross-linking agents, resins, crystallization inhibitors, and clays.

Such optional emulsifying agents, auxiliary emulsifying agents, surfactants and suspending agents may include, without limitation, one or more of monoglycerides, diglycerides, polyoxyl stearate, a mixture of triceteareth-4 phosphate with ethylene glycol palmitostearate and with diethylene glycol palmitostearate, polyglyceryl-3 diisostearate, a mixture of PEG-6 stearate with ethylene glycol palmitostearate and with PEG-32 stearate, oleoylpolyoxyl-6 glycerides, lauroyl polyoxyl-6 glycerides, caprylocaproyl polyoxyl-8 glycerides, propylene glycol monocaprylate type I, propylene glycol monolaurate type II, propylene glycol monolaurate type I, propylene glycol monocaprylate type II, polyglyceryl-3 dioleate, a mixture of PEG-6 stearate with PEG-32 stearate, lecithin, cetyl alcohol, cholesterol, bentonite, veegum, magnesium hydroxide, dioctyl sodium sulfosuccinate, sodium lauryl sulfate, triethanolamine stearate, potassium laurate, polyoxyethylene fatty alcohol ethers, glyceryl monostearate, polyoxyethylenepoloxypropylene block copolymers (poloxamers), sorbitan monolaurate, lanolin alcohols and ethoxylated lanolin alcohols, sorbitan fatty acid esters, sucrose distearate, sodium alginate, alginic acid, hectorite, aluminum silicate, polysorbate (e.g. polysorbate 20, polysorbate 40, polysorbate 60, polysorbate 80 etc.), and Span® surfactant products (e.g., Span® 80, Span® 20).

Emollients, humefactant, demulcents and skin irritation reducing agents may be selected from, without limitation, one or more of glycerin, propylene glycol, mineral oil, petrolatum, lanolin, paraffin, cetyl alcohol, cetyl esters wax, zinc oxide, and dimethicone.

Preservatives and stabilizers may be selected from, without limitation, one or more of sodium metabisulfite, citric acid, ascorbic acid, vitamin E, butylated hydroxyanisole (BHA), butylated hydroxyltoluene (BHT), alpha tocopherol, acorbyl palmitate, propionic acid, sodium bisulfate, propyl gallate, monothioglycerol, sodium ascorbate, benzethoniumchloride, chlorhexidine, phenylethyl alcohol, chloroxylenol, cresol, hexetidine, phenoxyethanol, chlorobutanol, ascorbic acid, benzoic acid, sodium benzoate, sorbic acid, potassium sorbate, potassium metabisulfite, phenol, potassium benzoate, dehydroacetic acid, cetylpyridinium chloride, methylparaben, propylparaben, butylparaben, benzyl alcohol, benzalkonium chloride, and discoloring agents.

Chelating agents may be selected from, without limitation, one or more of sodium edetate, edetic acid, tartaric acid, fumaric acid, disodium edetate, trisodium edetate, dipotassium edetate).

Fillers may be selected from, without limitation, one or more of lactose, magnesium stearate, mannitol, starch, sugars, titanium dioxide, talc, shellac, colloidal silicone dioxide, kaolin, magnesium oxide, clays.

Many suitable methods and corresponding materials to make the patches described herein are known in the art. According to an embodiment of the present invention, a patch may be formed, for example, without limitation, by solvent casting onto a backing layer or release liner, and sandwiching between both, as described herein.

Many suitable materials for the backing layer are known, and include polymer films, fabrics and non-woven materials, e.g. continuous films that prevent ingress of external moisture into the adhesive layer from activities such as showering or bathing. The backing layer should preferably be occlusive, or substantially occlusive. However, based on delivery mechanism, non-occlusive backings may be functional. Such films include, without limitation, polypropylene, polyvinyl chloride, cellulose acetate, ethyl cellulose, polyurethane, polyethylene, polyvinyl acetate, polyester, copolymers, and combinations thereof. Optionally, the backing may be a layered composite that include a metal, such as, without limitation aluminum, e.g. polyethylene terephthalate-aluminium-polyethylene composites, or e.g. a polyester and an ethylene vinyl acetate copolymer heat seal layer (particularly as a backing), or e.g. a fluoropolymer coated polyester film (particularly as a release liner. Suitable backing layers include, without limitation, Scotchpak 1006, 1022, 1109, 9723, 9732, 9733 (3M company).

Many suitable materials for the release liner are known, and include paper, polymer film materials. The release liner is removable and disposable prior to application of a transdermal system. Release liners are typically coated with a release coating selected from the group consisting of fluorocarbon, fluorosilicone, PTFE or silicone. They may also be extruded, co-extruded, or otherwise combined with a release agent in place of a coating. Such films include, without limitation, polypropylene, polystyrene, polyvinyl chloride, cellulose acetate, ethyl cellulose, polyurethane, polyethylene, polyvinyl acetate, polyester, copolymers, and combinations thereof. Optionally, the backing may be a layered composite that include a metal, such as, without limitation aluminum, vapor coated or vapor deposited aluminum. Suitable release liners include, without limitation, 3M Scotchpak 1022, 9709, 9741, 9742, 9744, and 9755 (3M company).

Non-limiting exemplary embodiments are disclosed below

1. A method of treating multiple myeloma, transfusion-dependent anemia due to low- or intermediate-1-risk myelodysplastic syndromes, mantle cell lymphoma, chronic lymphocytic leukemia, hematologic cancers, solid tumor cancers, or inflammatory disease comprising: continuously administering to a subject in need of the treatment a formulation comprising an immunomodulatory imide compound and a pharmaceutically acceptable carrier.

2. The method of embodiment 1, wherein the method continuously administers the formulation to achieve an AUC of the immunomodulatory imide compound of between 10% and 60% of the exposure (AUC) obtained from a standard of care treatment, or wherein the method continuously administers the formulation at a dose rate such that the daily dose of the immunomodulatory imide compound is 10-75% of the daily dose of a standard of care treatment.

3. The method of embodiment 1 or 2, wherein the method continuously administers the formulation to achieve a blood level of the immunomodulatory imide compound that is equivalent to the blood level at a time point from 10 hours to 16 hours obtained from once daily oral dose of 2.5-50 mg of the immunomodulatory imide compound.

4. The method of embodiment 3, wherein the method continuously administers the formulation to achieve a blood level of the immunomodulatory imide compound that is equivalent to the blood level at 12 hours obtained from once daily oral dose of 2.5-50 mg of the immunomodulatory imide compound.

5. The method of any of the preceding embodiments, wherein continuous administration of the formulation comprising the immunomodulatory imide compound and the pharmaceutically acceptable carrier comprises continuous administration of the formulation to the subject for one day, two days, three days, four days, five days, six days, seven days, eight days, nine days, ten days, eleven days, twelve days, thirteen days, or fourteen days 6. The method of any of the preceding embodiments, wherein the immunomodulatory imide compound is selected from the group consisting of thalidiomode, lenalidomide, pomalidomide, apremilast, and iberdomide.

7. The method of embodiment 6, wherein the immunomodulatory imide compound is lenalidomide.

8. The method of embodiment 7, wherein the continuous administration comprises continuous administration of lenalidomide to the subject at a rate of about 16-1400 µg/hour.

9. The method of embodiment 7, wherein continuous administration comprises continuous administration of the formulation to the subject to achieve a steady state plasma level of lenalidomide in a range of about 3.5-140 µg/L.

10. The method of embodiment 7, wherein lenalidomide is continuously delivered at a rate of 185 µg to 725 µg/hour for treating newly diagnosed multiple myeloma.

11. The method of embodiment 10, wherein the method achieves a steady state blood level of lenalidomide in the range of about 19-70 µg/L.

12. The method of embodiment 7, wherein lenalidomide is continuously delivered at a rate of 70 µg to 285 µg/hour for maintenance treatment of multiple myeloma.

13. The method of embodiment 12, wherein the method achieves a steady state blood level of lenalidomide in the range of about 7.5-28 µg/L.

14. The method of embodiment 7, wherein lenalidomide is continuously delivered at a rate of 30 µg to 145 µg/hour for treating chronic lymphocytic leukemia.

15. The method of embodiment 14, wherein the method achieves a steady state blood level of lenalidomide in the range of about 3.5-14 µg/L.

16. The method of any of the preceding embodiments, wherein the method comprises continuously administering the formulation to the subject via infusion.

17. The method of any of the preceding embodiments, wherein the method comprises continuously administering the formulation to the subject via intravenous or subcutaneous infusion.

18. The method of any of the preceding embodiments, wherein the method comprises continuously administering the formulation to the subject via subcutaneous infusion.

19. The method of any of the preceding embodiments, wherein the pharmaceutically acceptable carrier comprises water, carboxymethyl cellulose (CMC), Tween 80, dimethyl sulfoxide (DMSO), ethanol, 2-hydroxypropyl-β-cyclodextrin, dextrose, PEG400, or combinations thereof.

20. The method of embodiment 19, wherein the pharmaceutically acceptable carrier comprises water and PEG 400.

21. The method of embodiment 20, wherein the pharmaceutically acceptable carrier comprises water and PEG 400 at a ratio of 5:1 (v/v).

22. The method of any of embodiments 1-15, wherein the formulation is in the form of a transdermal formulation, extended or sustained release tablet or capsule, or implant.

23. The method of embodiment 22, wherein the transdermal formulation comprises a transdermal liquid formulation, a transdermal semisolid formulation, a transdermal polymer matrix formulation, or combinations thereof.

24. The method of embodiment 22, wherein the transdermal formulation is in the form of a transdermal patch.

25. The method of embodiment 24, wherein the transdermal patch is selected from the group consisting of a reservoir patch, a microreservoir patch, a matrix patch, a pressure sensitive adhesive patch, and an extended release transdermal film.

26. The method of embodiment 22, wherein the transdermal formulation is in the form of a liquid formulation and/or semisolid formulation.

27. The method of embodiment 22, wherein the transdermal formulation is for delivery using microneedles.

28. The method of any of embodiments 22-27, wherein the administration step comprises administering the formulation to a subject once every two days, once every three days, once every four days, once every five days, once every six days, once every seven days, or once every ten days for a predetermined time period.

29. The method of any of embodiments 22-28, further comprising the step of:
   b. obtaining a blood sample of the subject after the step of applying the formulation;
   c. performing a pharmacokinetic assessment of the blood sample;
   d. adjusting the transdermal formulation in response to the pharmacokinetic assessment; and
   e. applying the adjusted formulation to the subject.

Various formulations of immunomodulatory imide compounds for administration are prepared as described in the general embodiments of various platforms below.

An embodiment of an extended or sustained release tablet or capsule formulation for oral administration comprising:
   an immunomodulatory imide compound,
   a thickening polymer, alone or in combination,
   a film forming polymer, alone or in combination,
   a binder, filler, lubricant, stabilizer, solubilizer, surfactant, alone or in combination,
which are combined by a specified process and compressed into a tablet or filled into a capsule for oral administration.

An embodiment of patch formulation for transdermal or topical administration comprising.
   an immunomodulatory imide compound,
   a pressure sensitive adhesive, alone or in combination,
   a polymer, enhancer, binder, filler, lubricant, stabilizer, solubilizer, surfactant, alone or in combination,
   a backing layer, occlusive or non-occlusive,
   a release liner, removable and disposable,
which are combined in a specified process and adhesive matrix is laminated between the backing layer and release liner for storage of adhesive patch in a pouch prior to use by application of patch to the skin of a subject.

An embodiment of an implant comprising
   an immunomodulatory imide compound,
   a hot melt polymer, alone or in combination,
   a polymer, enhancer, binder, filler, lubricant, stabilizer, solubilizer, surfactant, alone or in combination,
which are combined in a specified process and stored in a pouch prior to use by implantation into a subject for administration.

SPECIFIC EXAMPLES

Example 1: Efficacy of Lenalidomide Continuous Infusion in Myeloma Xenograft Model Six groups of female CB.17 SCID mouse, each containing ten mice, were subcutaneously injected with $1 \times 10^7$ H929 multiple myeloma tumor cells in 50% Matrigel. After the tumor reached an average size of 100-150 mm$^3$, an iPrecio pump was surgically implanted into each of the mice. Dosing began twenty-four hours post pump implantation. Group 1, the control group, was treated with vehicle via intraperitoneal injection once a day. Group 2 was treated with lenalidomide via intraperitoneal injection once a day. Each of Groups 3-6 was treated lenalidomide via continuous subcutaneous infusion at different hourly rate. The dosing lasted 14 days followed by one day off the treatment and lasted for another 14 days. The iPrecio pump was replaced after 14 days. The formulation used in Groups 2-6 contains 20% PEG400 in water as the carrier. Blood was drawn at predetermined time points and analyzed The table below lists the daily dose and schedule for each of the six groups.

| Gr. | N | Agent | Active dose (daily) | Active dose (hourly) | iPrecio Pump Flow Rate | Route | Schedule |
|---|---|---|---|---|---|---|---|
| 1[#] | 10 | vehicle | na | na | Na | ip | qd × 14/1 day off/qd × 14 |
| 2 | 10 | lenalidomide | 25 mg/kg[1] | na | Na | ip | qd × 14/1 day off/qd × 14 |
| 3 | 10 | lenalidomide | 144 μg/day | 6 μg/hr | 4 μL/hr | sc iPrecio pump | continuous for 14 days/1 day off/ continuous for 14 days |
| 4 | 10 | lenalidomide | 48 μg/day | 2 μg/hr | 4 μL/hr | sc iPrecio pump | continuous for 14 days/1 day off/ continuous for 14 days |
| 5 | 10 | lenalidomide | 24 μg/day | 1 μg/hr | 4 μL/hr | sc iPrecio pump | continuous for 14 days/1 day off/ continuous for 14 days |
| 6 | 10 | lenalidomide | 12 μg/day | .5 μg/hr | 4 μL/hr | sc iPrecio pump | continuous for 14 days/1 day off/ continuous for 14 days |

[1]The mice weighed 20 g on average, the daily dose of 25 mg/kg corresponds to 500 μg/day.

Figure 2:
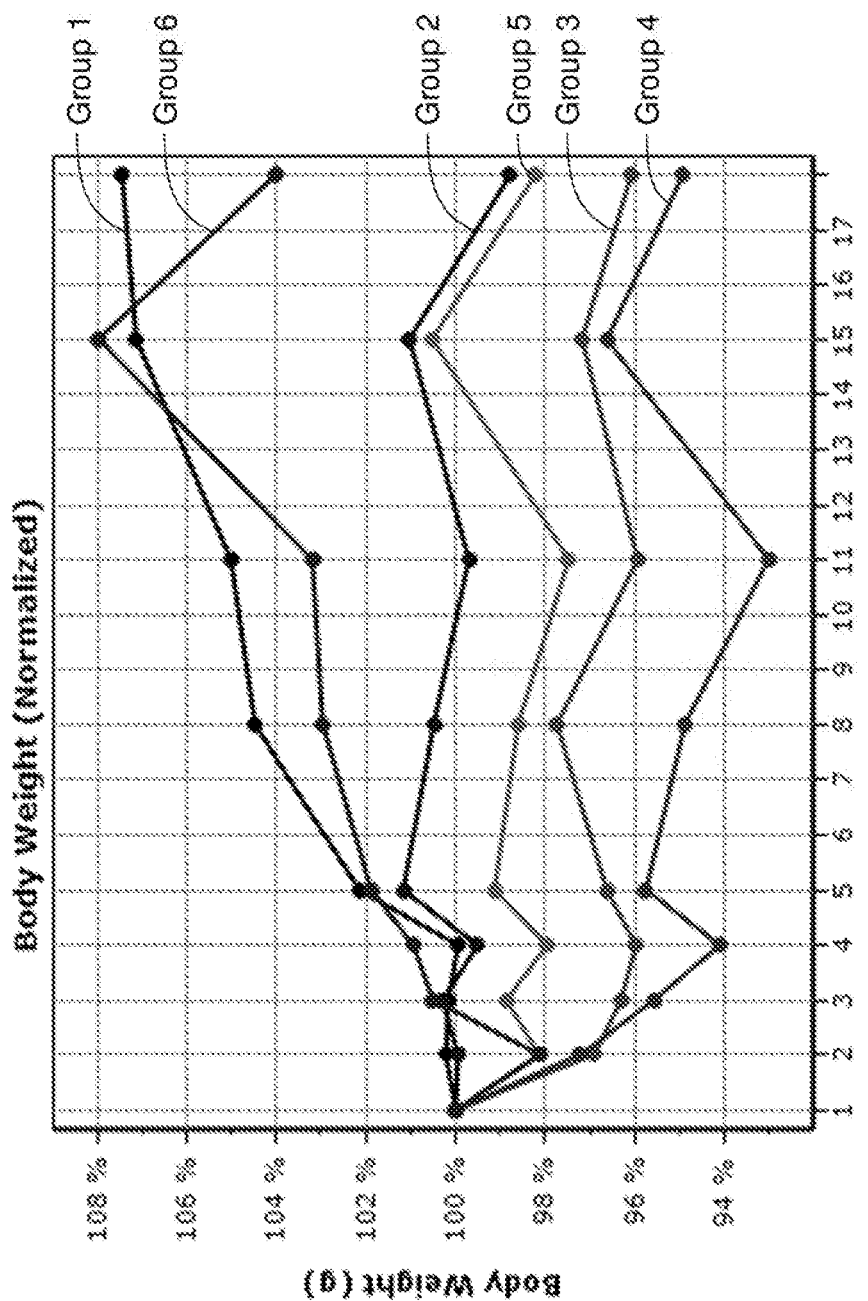
FIG. 2 demonstrates the body weight as a function of time, in days post continuous administration of lenalidomide at various hourly rate (μg/hour) comparing with a vehicle and intraperitoneal injection of lenalidomide once a day.

FIG. 1 displays the normalized tumor volume as a function of time, in days post the treatment (day 1 is the day when the treatment begins) for each of the six groups. Group 3 with the daily dose of 144 μg of lenalidomide via continuous subcutaneous infusion is the only group having tumor volume reduced during the treatment schedule. Group 2 with a much higher daily dose, i.e., 500 μg of lenalidomide, via Intraperitoneal injection failed to inhibit the growth of the tumor volume. FIG. 2 displays the normalized body weight as a function of time, in days post the treatment (day 1 is the day when the treatment begins). Group 3 had insignificant weight loss.

Figure 7:
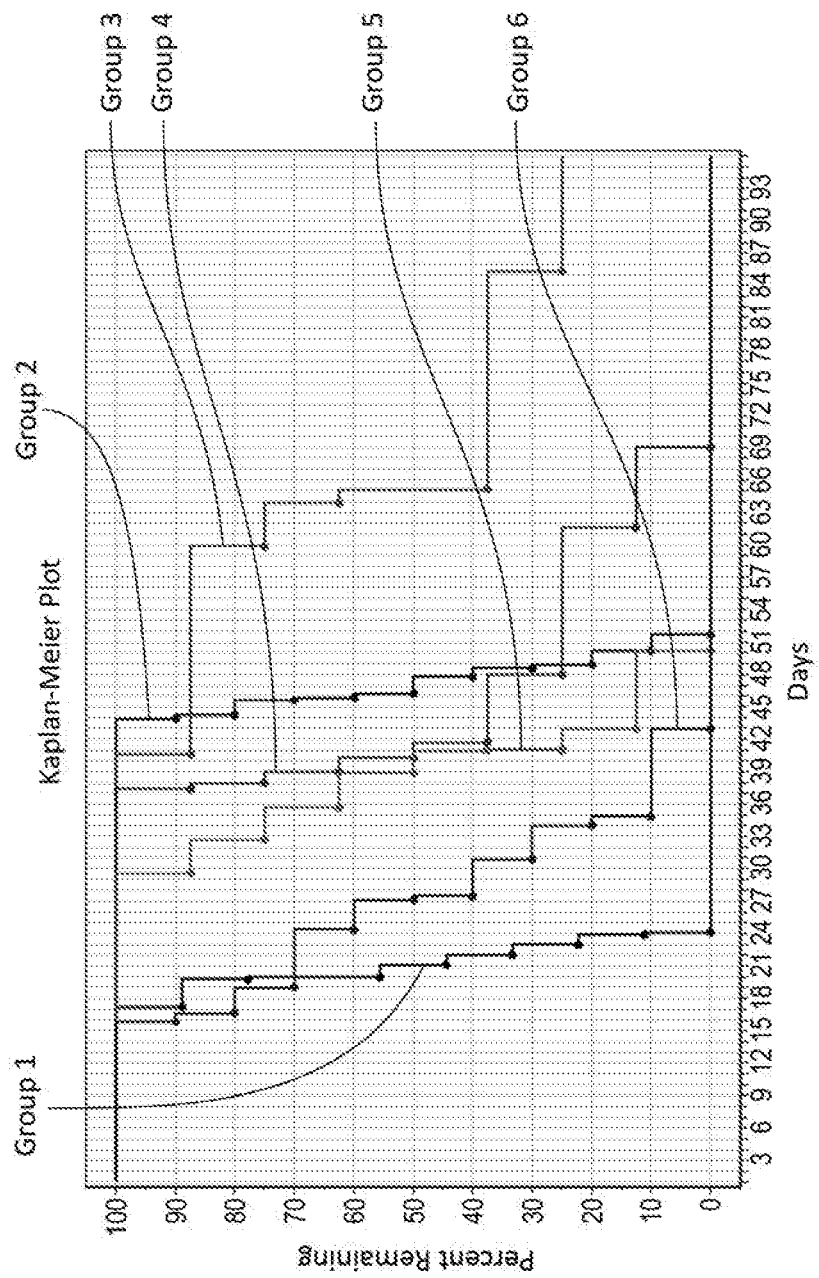
FIG. 7 is a Kaplan-Meier Plot displaying the survival percentages of mice xenografted with multiple myeloma as a function of time, in days post continuous administration of lenalidomide at various hourly rate (μg/hour) comparing with a vehicle and intraperitoneal injection of lenalidomide once a day.

FIG. 7, a Kaplan-Meier Plot, displays the survival percentage of the mice as a function of time, in day 1 to day 95 post the treatment (day 1 is the day when the treatment begins) for each of the six groups. Group 3 with the daily dose of 144 μg of lenalidomide via continuous subcutaneous infusion is the only group having mice survived for 95 days. Group 2 with a much higher daily dose, i.e., 500 μg of lenalidomide, via Intraperitoneal injection failed to inhibit the growth of the tumor volume and has no mouse survived at day 52.

Table 1 below lists the white blood cell count (WBC), platelet count (PLT), and absolute neutrophil count (ANC) for each group at day 8 post the treatment, which indicates no substantial hematologic toxicity for Groups 3-6.

TABLE 1

WBC, PLT, and ANC for each group at day 8 post the treatment

| Gr. | WBC ($10^3$ cells/μL) (normal range: 1.4-5.4) | PLT ($10^3$ cells/μL) (normal range: 733-1441) | ANC ($10^3$ cells/μL) (normal range: 0.77-2.5) |
|---|---|---|---|
| 1 | 1.9 | 830 | 1.3 |
| 2 | 1.8 | 850 | 1.2 |
| 3 | 2.8 | 1360 | 2.4 |
| 4 | 2.4 | 1345 | 1.9 |
| 5 | 3.3 | 1410 | 2.8 |
| 6 | 3.2 | 1535 | 2.5 |

The multiple myeloma study in SCID mice provides pharmacokinetically modeled data to support three treatment paradigms. The standard of care treatment in the mouse model study is a daily intraperitoneal dose of 500 mcg administered once a day (see Group 2). This produced blood levels at Cmax of 2.9 mcg/mL and a trough of 0.002 mcg/mL. The range of tolerable and effective blood levels ranged from the blood level at 10 hours to the blood level at 16 hours. Continuous blood levels of greater than those observed at 8 hours or 0.29 mcg/mL and lower than those observed at 18 hours or 0.013 mcg/mL were either toxic or ineffective, respectfully. The maintenance of continuous dose specific blood levels in terms of their time range are predicted to be safe and effective and result in activity in humans.

Example 2: Preparing a Lenalidomide Topical Formulation

A lenalidomide formulation is prepared by mixing a pharmaceutically acceptable form of lenalidomide, with one or more excipients (or enhancers), and a solvent. The proportions of each by % w/w are shown below.

| Formulation | % w/w |
|---|---|
| lenalidomide | 1-95% |
| Excipient 1 | 0-95% |
| Excipient 2 | 0-95% |
| Solvent | 1-95% |
| Total | 100 |

Example 3: Forming a Pomalidomide Topical Formulation

A pomalidomide formulation is prepared by mixing a pharmaceutically acceptable form of pomalidomide, with one or more excipients ((or enhancers), and a solvent. The proportions of each by % w/w are shown below.

| Formulation | % w/w |
|---|---|
| pomalidomide | 1-95% |
| Excipient 1 | 0-95% |
| Excipient 2 | 0-95% |
| Solvent | 1-95% |
| Total | 100 |

Example 4: Forming a Thalidomide Topical Formulation

A thalidomide formulation is prepared by mixing a pharmaceutically acceptable forms of thalidomide, with one or more excipients (or enhancers), and a solvent. The proportions of each by % w/w are shown below.

| Formulation | % w/w |
|---|---|
| thalidomide | 0.5-95% |
| Excipient 1 | 0-95% |
| Excipient 2 | 0-95% |
| Solvent | 1-95% |
| Total | 100 |

Example 5: Preparation of a Transdermal Patch

A patch may be formed from a drug-in-adhesive polymer blend by casting the material onto a release liner, curing the adhesive and laminating the adhesive to a backing layer. The resulting laminate may be die cut into a fixed area patch.

| Formulation | % w/w |
|---|---|
| lenalidomide | 0.5-95% |
| Pressure sensitive adhesive/ Polymer | 0-95% |
| Excipient 1 | 0-95% |
| Excipient 2 | 0-95% |
| Process Solvent | 1-95% |
| Total | 100% |

Figure 3:
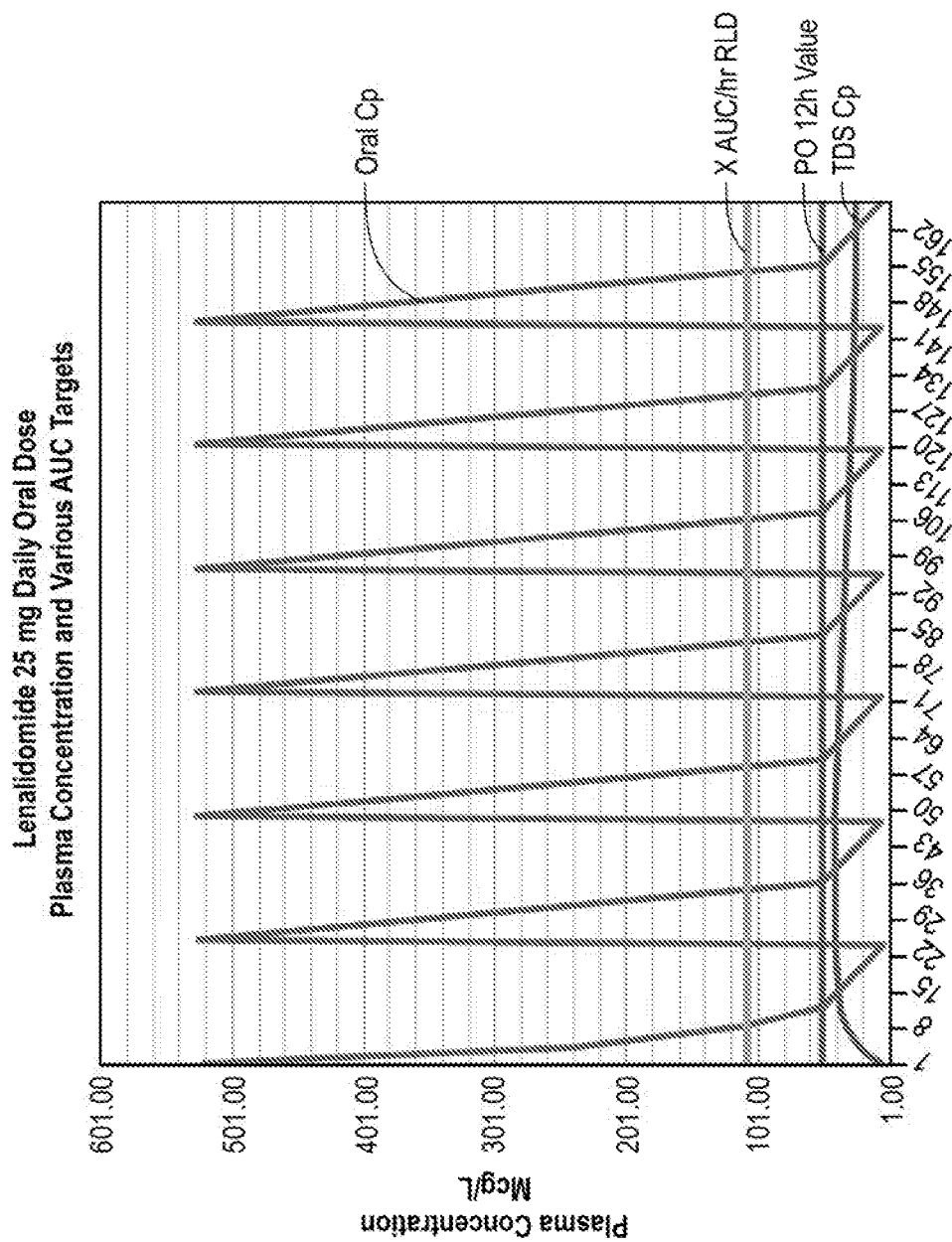
FIGS. 3 and 4 demonstrates plasma concentration of lenalidomide 25 mg daily oral dose compared to three continuous delivery rates.

Example 6: Blood Plasma Concentration (1)—Based on 25 mg Lenalidomide Once Daily Orally A standard lenalidomide dose of 25 mg orally once a day is used to calculate the pharmacokinetic profile for the projected blood levels of lenalidomide over 7 days of dosing. As shown in FIG. 3, the lenalidomide blood levels of the oral dose (as shown in the Oral Cp-line) range from a Cmax of 522 to a Cmin of 5.2 mcg/L over the dose interval of 24 hours. The area of the time concentration curve (AUC) calculated by the trapezoidal rule is 2609 mcg/L/hr for the interval 0-24 hours. The plasma concentration associated with the arithmetic mean of the hourly AUC over the dose interval is 108 mcg/L (mean (X) AUC/hr RLD line). That is, a constant blood level of 108 mcg/L would produce the same drug exposure over time exhibited by the oral dose regimen, but without the high peak and low trough. A second method of establishing an AUC target is to identify the blood level (mcg/L) point estimate with oral administration where half of the dose interval is above the point estimate and half of the dose interval is below the point estimate. In this example, the blood level at the mid-point of the 24-hour dosing interval is 52 mcg/L (PO 12 h Value line). Further, in this example, the TDS flux blood levels which might be targeted is determined from experimental data where efficacy is maintained but toxicity is lower than the oral treatment.

In one example, the target blood concentration for the TDS delivery would be around 108 mcg/L to provide the same drug exposure as an oral dosing regimen at 25 mg a day. In this example the TDS would provide an equivalent AUC 2600 mcg/L/hr as the oral daily AUC.

In a second example, the target blood concentration for the TDS delivery would be around 52 mcg/L to provide the drug exposure equivalent to the mid-point of the dosing interval observed with an oral dosing regimen at 25 mg a day. In this example the TDS would provide an AUC of 1248 mcg/L/hr.

In a third example, the target blood concentration for the TDS delivery would be based on a lenalidomide dose of 15 mg every other day which is commonly used in the presence of hematologic toxicity and is still considered effective. At this dose, the AUC of lenalidomide over 48 hours is 1536 mcg/L/hr with an average blood level of 32 mcg/L. The TDS blood level over the dosing period would approximate the 32 mcg/L plasma concentration at its zenith TDS Cp line).

Example 7: Blood Plasma Concentration (2)—Based on 25 mg Lenalidomide Once Daily Orally The first line treatment of multiple myeloma usually involves the administration of lenalidomide at dose of 25 mg a day orally. That treatment regimen results in maximum plasma concentrations of ~500 mcg/L at the Cmax of 1 hour and trough values of ~4 mcg/L at 24 hours. In this embodiment, continuous administration of lenalidomide from 697 mcg/hour (10 hour equivalent) to 191 mcg/hr (16 hour equivalent) represent the effective and safe range for the treatment of first line primary therapy in multiple myeloma in adults (See the table below). The blood level targets range from a low of 19.1 mcg/L to a high of 69.7 mcg/L. In one embodiment, the blood level target is 45 mcg/L (12 hour equivalent) produced by the continuous administration of 453 mcg/hr. In the way, the actual daily dose of lenalidomide is reduced by 56% compared to a once a day 25 mg pulsatile daily dose. Also, the total exposure in a weekly continuous administration treatment cycle compared to once daily dosing for 7 days measured in area-under-the-time-concentration-curve ($AUC_{0-168}$) is 68% lower than that observed with oral dosing of lenalidomide.

| Blood level and dose ranges of continuously administered lenalidomide in adults at a biologically equivalent dose to once daily lenalidomide at 25 mg a day | | | |
|---|---|---|---|
| TEMPORAL EQUIVALENT BLOOD LEVEL WITH A 25 MG DOSE | 10 hr | 12 hr | 16 hr |
| STEADY STATE PLASMA LEVEL MCG/L | 69.7 | 45.3 | 19.1 |
| AVERAGE DOSE NEEDED MCG/HR | 697 | 453 | 191 |
| DOSE/DAY MCG | 16729 | 10861 | 4577 |
| % DOSE OF ORAL | 67% | 43% | 18% |
| AUC MCG/L/HR | 17718 | 7087 | 2045 |
| % AUC OF ORAL | 49% | 32% | 13% |

Figure 4:
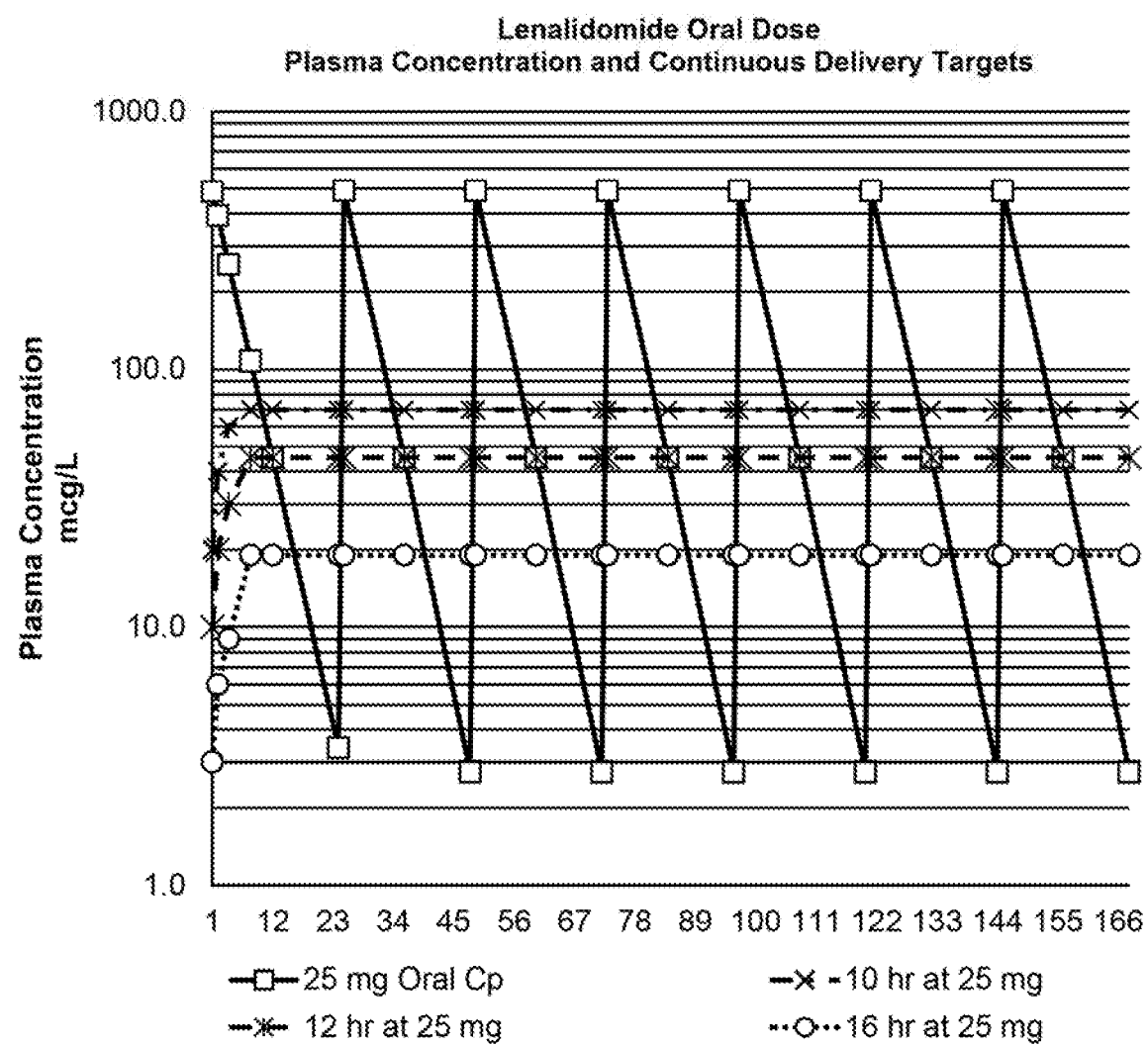

The graphic representation of the plasma concentration over time curves of a weekly cycle of lenalidomide for this embodiment are provided in FIG. 4. FIG. 4 displays blood levels of pulsatile and continuous lenalidomide emulating a once daily 25 mg oral dose compared to 3 unique continuous infusion rates.

Example 8: Blood Plasma Concentration (3)—Based on 10 mg Lenalidomide Once Daily Orally The maintenance treatment of multiple myeloma usually involves the administration of lenalidomide at dose of 10 mg a day orally. That treatment regimen results in maximum plasma concentrations of ~200 mcg/L at the Cmax of 1 hour and trough values of ~1.4 mcg/L at 24 hours. In this embodiment, continuous administration of lenalidomide from 279 mcg/hour (10 hour equivalent) to 76 mcg/hr (16 hour equivalent) represent the effective and safe range for the treatment of first line maintenance therapy in multiple myeloma in adults (See the table below). The blood level targets range from a low of 7.6 mcg/L to a high of 27.9 mcg/L. In one embodiment, the blood level target is 18.1 mcg/L produced by the continuous administration of 181 mcg/hr (12 hour equivalent). In this way, the actual daily dose of lenalidomide is reduced by 57% compared to a once a day 10 mg pulsatile daily dose. Also, the total exposure in a weekly continuous administration treatment cycle compared to once daily dosing for 7 days measured in area-under-the-time-concentration-curve ($AUC_{0\text{-}168}$) is 68% lower than that observed with oral dosing of lenalidomide.

| Blood level and dose ranges of continuously administered lenalidomide in adults at a biologically equivalent dose to once daily lenalidomide at 10 mg a day | | | |
|---|---|---|---|
| TEMPORAL EQUIVALENT BLOOD LEVEL WITH A 10 MG DOSE | 10 hr | 12 hr | 16 hr |
| STEADY STATE PLASMA LEVEL MCG/L | 27.9 | 18.1 | 7.6 |
| AVERAGE DOSE NEEDED MCG/HR | 279 | 181 | 76 |
| DOSE/DAY MCG | 6692 | 4344 | 1831 |
| % DOSE OF ORAL | 67% | 43% | 18% |
| AUC MCG/L/HR | 4609 | 2984 | 1253 |
| % AUC OF ORAL | 49% | 32% | 13% |

Figure 5:
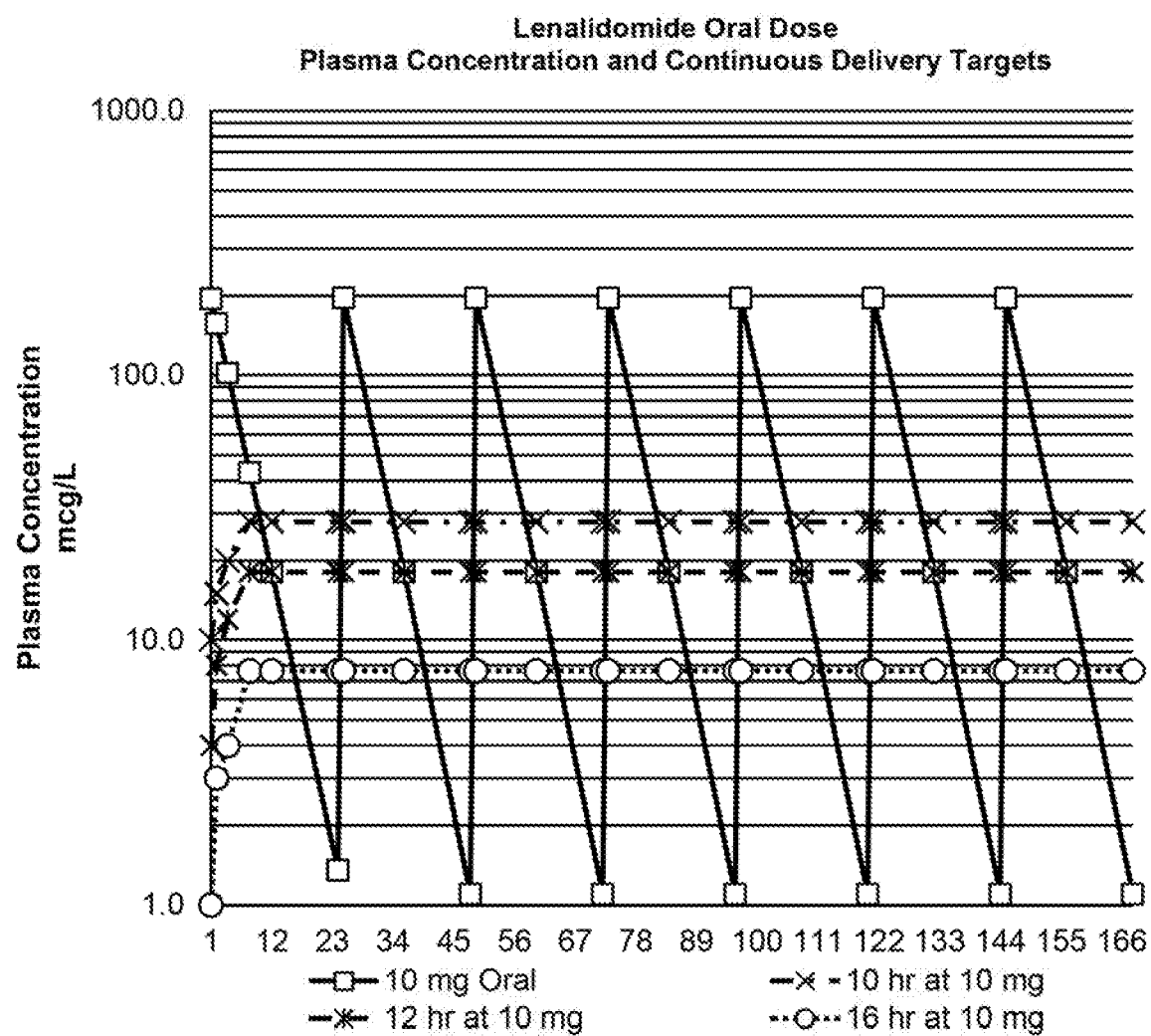
FIG. 5 demonstrates plasma concentration of lenalidomide 10 mg daily oral dose compared to three continuous delivery rates.

The graphic representation of the plasma concentration over time curves of a weekly cycle of lenalidomide for this embodiment are provided in FIG. 5. FIG. 5 displays blood levels of pulsatile and continuous lenalidomide emulating a once daily 10 mg oral dose compared to 3 unique continuous infusion rates.

Example 9: Blood Plasma Concentration (4)—Based on 5 mg Lenalidomide Once Daily Orally The treatment of chronic lymphocytic leukemia (CLL) usually involves the administration of lenalidomide at dose of 5 mg a day orally. That treatment regimen results in maximum plasma concentrations of ~100 mcg/L at the Cmax of 1 hour and trough values of ~0.6 mcg/L at 24 hours. In this embodiment, continuous administration of lenalidomide from 139 mcg/hour (10 hour equivalent) to 38 mcg/hr (16 hour equivalent) represent the effective and safe range for the treatment of CLL in adults (See the table below). The blood level targets range from a low of 3.8 mcg/L to a high of 13.9 mcg/L. In one embodiment, the blood level target is 9.1 mcg/L (12 hour equivalent) produced by the continuous administration of 91 mcg/hr. In this way, the actual daily dose of lenalidomide is reduced by 58% compared to a once a day 5 mg pulsatile daily dose. Also, the total exposure in a weekly continuous administration treatment cycle compared to once daily dosing for 7 days measured in area-under-the-time-concentration-curve ($AUC_{0\text{-}168}$) is 68% lower than that observed with oral dosing of lenalidomide.

| Blood level and dose ranges of continuously administered lenalidomide in adults at a biologically equivalent dose to once daily lenalidomide at 5 mg a day | | | |
|---|---|---|---|
| TEMPORAL EQUIVALENT BLOOD LEVEL WITH A 5 MG DOSE | 10 hr | 12 hr | 16 hr |
| STEADY STATE PLASMA LEVEL MCG/L | 13.9 | 9.1 | 3.8 |
| AVERAGE DOSE NEEDED MCG/HR | 139 | 91 | 38 |
| DOSE/DAY MCG | 3346 | 2172 | 915 |
| % DOSE OF ORAL | 67% | 43% | 18% |
| AUC MCG/L/HR | 2310.4 | 1498.2 | 626.7 |
| % AUC OF ORAL | 50% | 32% | 14% |

Figure 6:
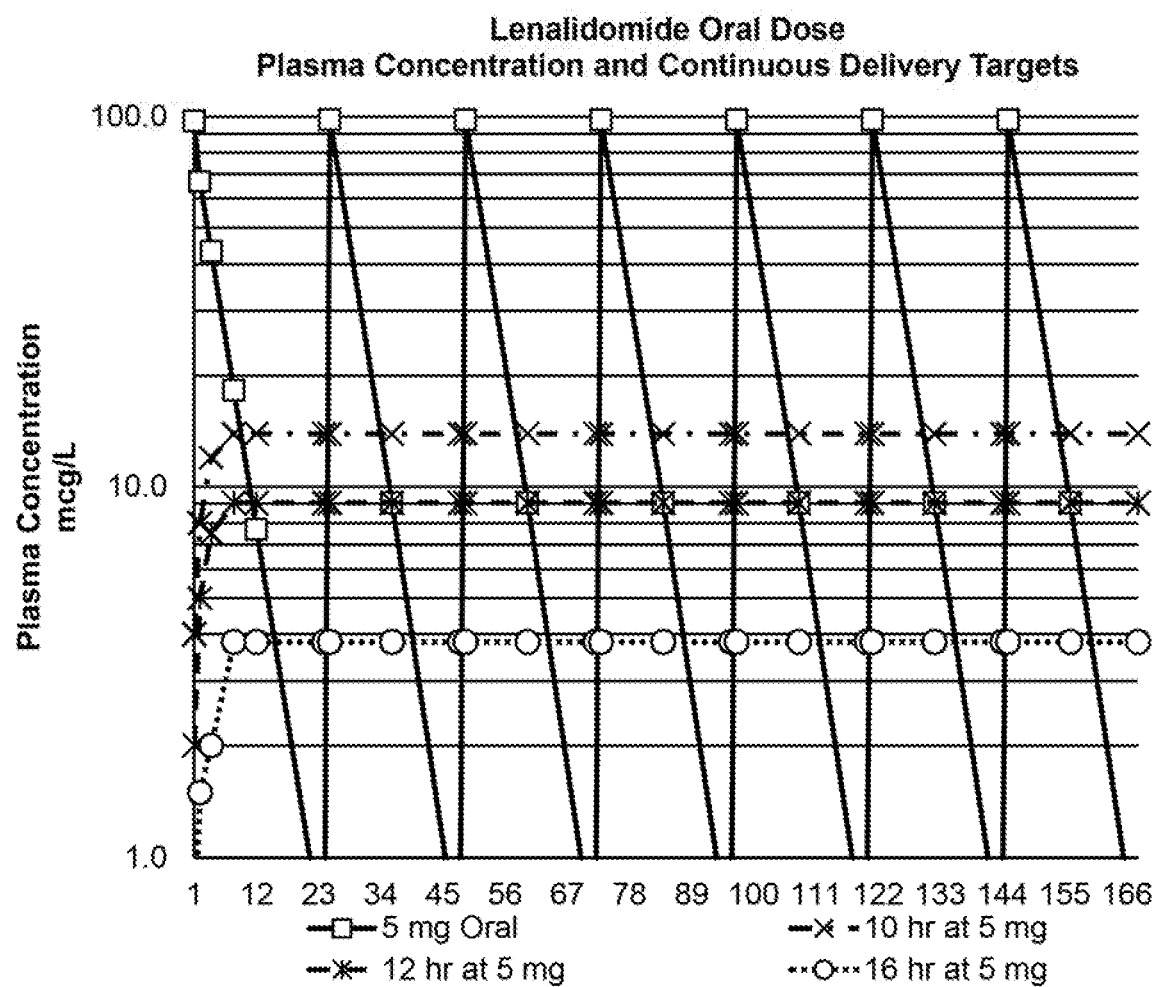
FIG. 6 demonstrates plasma concentration of lenalidomide 5 mg daily oral dose compared to three continuous delivery rates.

The graphic representation of the plasma concentration over time curves of a weekly cycle of lenalidomide for this embodiment are provided in FIG. 6. FIG. 6 displays blood levels of pulsatile and continuous lenalidomide emulating a once daily 5 mg oral dose compared to 3 unique continuous infusion rates.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature rather than restrictive.

What is claimed:

1. A method of treating multiple myeloma, transfusion-dependent anemia due to low- or intermediate-1-risk myelodysplastic syndromes, mantle cell lymphoma, chronic lymphocytic leukemia, hematologic cancers, solid tumor cancers, or inflammatory disease comprising: continuously administering to a subject in need of the treatment a formulation comprising an immunomodulatory imide compound and a pharmaceutically acceptable carrier, wherein the immunomodulatory imide compound is selected from the group consisting of thalidomide and its analogues, and wherein the method comprises continuously administering the formulation to the subject via subcutaneous infusion from an external drug supply.

2. The method of claim 1, wherein the method continuously administers the formulation to achieve an AUC of the immunomodulatory imide compound of between 10% and 60% of the exposure (AUC) obtained from a standard of care treatment, or wherein the method continuously administers the formulation at a dose rate such that the daily dose of the immunomodulatory imide compound is 10-75% of the daily dose of a standard of care treatment, wherein the standard of care treatment is an oral dose of 2.5-50 mg of the immunomodulatory compound once daily.

3. The method of claim 1, wherein the method continuously administers the formulation to achieve a blood level of the immunomodulatory imide compound that is equivalent to the blood level at a time point from 10 hours to 16 hours obtained from once daily oral dose of 2.5-50 mg of the immunomodulatory imide compound.

4. The method of claim 3, wherein the method continuously administers the formulation to achieve a blood level of the immunomodulatory imide compound that is equivalent to the blood level at 12 hours obtained from once daily oral dose of 2.5-50 mg of the immunomodulatory imide compound.

5. The method of claim 1, wherein continuous administration of the formulation comprising the immunomodulatory imide compound and the pharmaceutically acceptable carrier comprises continuous administration of the formulation to the subject for one day, two days, three days, four days, five days, six days, seven days, eight days, nine days, ten days, eleven days, twelve days, thirteen days, or fourteen days.

6. The method of claim 1, wherein the immunomodulatory imide compound is selected from the group consisting of lenalidomide, pomalidomide, and iberdomide.

7. The method of claim 1, wherein the immunomodulatory imide compound is lenalidomide.

8. The method of claim 7, wherein the continuous administration comprises continuous administration of lenalidomide to the subject at a rate of about 16-1400 μg/hour.

9. The method of claim 7, wherein continuous administration comprises continuous administration of the formulation to the subject to achieve a steady state plasma level of lenalidomide in a range of about 3-140 μg/L.

10. The method of claim 7, wherein lenalidomide is continuously delivered at a rate of 185 μg to 725 μg/hour.

11. The method of claim 7, wherein the method achieves a steady state blood level of lenalidomide in the range of about 19-70 μg/L.

12. The method of claim 7, wherein lenalidomide is continuously delivered at a rate of 70 μg to 285 μg/hour.

13. The method of claim 7, wherein the method achieves a steady state blood level of lenalidomide in the range of about 7.5-28 μg/L.

14. The method of claim 7, wherein lenalidomide is continuously delivered at a rate of 30 μg to 145 μg/hour for treating chronic lymphocytic leukemia.

15. The method of claim 7, wherein the method achieves a steady state blood level of lenalidomide in the range of about 3-14 μg/L.

16. The method of claim 1, wherein the pharmaceutically acceptable carrier comprises water, n-methyl-2-pyrrolidone, polyvinylpyrrolidone, carboxymethyl cellulose (CMC), Tween 80, dimethyl sulfoxide (DMSO), ethanol, 2-hydroxypropyl-β-cyclodextrin, dextrose, PEG400, citric acid, sodium bicarbonate, or combinations thereof.

17. The method of claim 16, wherein the pharmaceutically acceptable carrier comprises water n-methyl-2-pyrrolidone, polyvinylpyrrolidone, citric acid, and sodium bicarbonate.

18. The method of claim 1, wherein a pump continuously administers the formulation to the subject.

* * * * *